US007867483B2

(12) United States Patent
Delcayre et al.

(10) Patent No.: US 7,867,483 B2
(45) Date of Patent: Jan. 11, 2011

(54) USE OF MVA TO TREAT PROSTATE CANCER

(75) Inventors: Alain Delcayre, San Jose, CA (US);
Reiner Laus, Saratoga, CA (US);
Stefanie Mandl, San Francisco, CA (US); Ryan Blair Rountree, San Jose, CA (US); Fatema Legrand, San Carlos, CA (US)

(73) Assignee: BN Immunotherapeutics, Inc., Mountain View, CA (US)

( * ) Notice: Subject to any disclaimer, the term of this patent is extended or adjusted under 35 U.S.C. 154(b) by 12 days.

(21) Appl. No.: 12/253,094

(22) Filed: Oct. 16, 2008

(65) Prior Publication Data

US 2009/0104225 A1 Apr. 23, 2009

Related U.S. Application Data

(60) Provisional application No. 60/960,893, filed on Oct. 18, 2007.

(51) Int. Cl.
*A61K 35/00* (2006.01)
*C12N 15/63* (2006.01)

(52) U.S. Cl. .................................. 424/93.1; 435/320.1

(58) Field of Classification Search .............. 435/320.1; 424/93.1, 232.1
See application file for complete search history.

(56) References Cited

U.S. PATENT DOCUMENTS

| 6,045,802 | A | * | 4/2000 | Schlom et al. | ............ 424/199.1 |
| 6,165,460 | A | * | 12/2000 | Schlom et al. | ............. 424/93.2 |
| 6,761,893 | B2 | | 7/2004 | Chaplin et al. | |
| 6,913,752 | B2 | | 7/2005 | Chaplin et al. | |
| 7,005,498 | B1 | | 2/2006 | Steinaa et al. | |
| 7,414,108 | B2 | | 8/2008 | Laus et al. | |

FOREIGN PATENT DOCUMENTS

| WO | WO 98/46769 A1 | 10/1998 |
| WO | WO03097845 A1 * | 11/2003 |
| WO | WO 2005/019464 A1 | 3/2005 |

OTHER PUBLICATIONS

Obasaju et al. Hematol-Oncol-Clin-North-Am. Jun. 2001; 15(3): 525-45, Abstract only.*
Mandl et al., MVA-BN-HER2: A Novel Vaccine for the Treatment of Breast Cancers Which Overexpress HER-2, J. Immunother. 29(6):652, 2006.
Mandl et al., MVA-BN-PRO: A Novel Immunotherapeutic for the Treatment of Prostate Cancer, J. Immunother. 30 (8):898, 2007.
Gulley et al., Phase I Study of a Vaccine Using Recombinant Vaccinia Virus Expressing PSA (rV-PSA) in Patients With Metastatic Androgen-Independent Prostate Cancer, The Prostate 53:109-117, 2002.
Eder et al., A Phase I Trial of a Recombinant Vaccinia Virus Expressing Prostate-specific Antigen in Advanced Prostate Cancer, Clinical Cancer Research 6:1632-1638, 2000.
Taichman et al., The evolving biology and treatment of prostate cancer, The Journal of Clinical Investigation 117, 2351-2361, 2007.
Webster et al., Prostate Cancer immunology: Biology, Therapeutics, and Challenges, Journal of Cinical Oncology 23, 8262-8269, 2005.
Harrop et al., Viral Vectors for Cancer Immunotherapy, Frontiers in Bioscience 11, 804-817, 2006.
Arlen et al., Pox Viral Vaccine Approaches, Semin Oncol 32:549-555, 2005.
Liu et al., Gene-based vaccines and immunotherapeutics, Proc. Natl. Acad. Sci. 101 (suppl. 2) 14567-14571, 2004.
Amato et al., 5T4-modified vaccinia ankara: progress in tumor-associated antigen-based immunotherapy, Expert Opin. Biol. Ther. 7(9):1463-1469, 2007.
Taichman et al., The evolving biology and treatment of prostate cancer, The Journal of Clinical Investigation 117 (9) 2351-2361, 2007.
Webster et al., Prostate cancer Immunology: Biology, Therapeutics, and Challenges, Journal of Clinical Oncology 23 (32) 8262-8269 (2005).
McNeel, Prostate cancer immunotherapy, Current Opinion in Urology 17:175-181, 2007.
Nelson, Prostate cancer prevention, Current Opinion in Urology 17:157-167, 2007.
Waeckerle-Men et al., Dendritic cell-based multi-epitope immunotherapy of hormone-refractory prostate carcinoma, Cancer Immunol Immunother 55: 1524-1533, 2006.
Machlenkin et al., Preventive and therapeutic vaccination with PAP-3, a novel human prostate cancer peptide, inhibits carcinoma development in HLA transgenic mice, Cancer Immunol Immunother 56:217-226, 2007.
Valone et al., Dendritic cell-based treatment of cancer: closing in on a cellular therapy, The Cancer Journal 7 (Suppl. 2):S53-61, 2001.
Fong et al., Induction of Tissue-Specific Autoimmune Prostatitis with Prostatic Acid Phosphatase Immunization, The Journal of Immunology 159: 3113-3117, 1997.
Fong et al., Dendritic Cell-Based Xenoantigen Vaccination for Prostate Cancer Immunotherapy, The Journal of Immunology 167: 7150-7156, 2001.
Johnson et al., Safety and immunological efficacy of a prostate cancer plasmid DNA vaccine encoding prostatic acid phosphatase (PAP), Vaccine 24: 293-303, 2006.
Johnson et al., Plasmid DNA vaccine encoding prostatic acid phosphatase is effective in eliciting autologous antigen-specific CD8+ T cells, Cancer Immunol Immunother 56:885-895, 2007.

* cited by examiner

*Primary Examiner*—Zachariah Lucas
*Assistant Examiner*—Bao Li
(74) *Attorney, Agent, or Firm*—Law Office of Salvatore Arrigo

(57) ABSTRACT

The invention relates to compositions, kits, and methods for cancer prophylaxis and therapy using recombinant MVA viruses encoding tumor-associated antigens, such as PSA and PAP. The recombinant MVA viruses can induce B- and T-cell responses. The recombinant MVA viruses can be administered prior to, at the same time as, or after a taxane.

13 Claims, 12 Drawing Sheets

SEQUENCE LISTING

```
<160> NUMBER OF SEQ ID NOS: 22

<210> SEQ ID NO 1
<211> LENGTH: 786
<212> TYPE: DNA
<213> ORGANISM: Homo sapiens

<400> SEQUENCE: 1
atgtgggtcc cggttgtctt cctcaccctg tccgtgacgt ggattggcgc tgcgcccctc      60
atcctgtctc ggattgtggg aggctgggag tgcgagaagc attcccaacc ctggcaggtg     120
cttgtggcct ctcgtggcag ggcagtctgc ggcggtgttc tggtgcaccc ccagtgggtc     180
ctcacagctg cccactgcat caggaacaaa agcgtgatct tgctgggtcg gcacagtctg     240
tttcatcctg aagacacagg ccaggtattt caggtcagcc acagcttccc acaccgctc      300 tacgatatga gcctcctgaa gaatcgattc ctcaggccag gtgatgactc cagccacgac     360
ctcatgctgc tccgcctgtc agagcctgcc gagctcacgg atgctgtgaa ggtcatggac     420
ctgcccaccc aggagccagc actggggacc acctgctacg cctcaggctg gggcagcatt     480
gaaccagagg agttcttgac cccaaagaaa cttcagtgtg tggacctcca tgttatttcc     540
aatgacgtgt gtgcgcaagt tcaccctcag aaggtgacca agttcatgct gtgtgctgga     600
cgctggacag ggggcaaaag cacctgctcg ggtgattctg ggggcccact tgtctgtaat     660
ggtgtgcttc aaggtatcac gtcatgggc agtgaaccat gtgccctgcc cgaaaggcct     720
tccctgtaca ccaaggtggt gcattaccgg aagtggatca aggacaccat cgtggccaac     780
ccctga                                                                786

<210> SEQ ID NO 2
<211> LENGTH: 1161
<212> TYPE: DNA
<213> ORGANISM: Homo sapiens
```

<400> SEQUENCE: 2

```
atgagagctg caccoctcct cctggccagg gcagcaagcc ttagccttgg cttcttgttt       60
ctgcttttt tctggctaga ccgaagtgta ctagccaagg agttgaagtt tgtgactttg      120
gtgtttcggc atggagaccg aagtcccatt gacacctttc ccactgaccc cataaaggaa     180
tcctcatggc cacaaggatt tggccaactc acccagctgg gcatggagca gcattatgaa     240
cttggagagt ataagaaa gagatataga aaattcttga atgagtccta taaacatgaa      300
caggtttata ttcgaagcac agacgttgac cggactttga tgagtgctat gacaaacctg     360
gcagccctgt tcccccaga aggtgtcagc atctggaatc ctatcctact ctggcagccc     420
atcccggtgc acacagttcc tctttctgaa gatcagttgc tatacctgcc tttcaggaac     480
tgccctcgtt ttcaagaact tgagagtgag actttgaaat cagaggaatt ccagaagagg     540
ctgcacccctt ataaggattt tatagctacc ttgggaaaac tttcaggatt acatggccag     600
gaccttttttg gaatttggag taaagtctac gaccctttat attgtgagag tgttcacaat     660
ttcactttac cctcctgggc cactgaggac accatgacta agttgagaga attgtcagaa     720
ttgtccctcc tgtccctcta tggaattcac aagcagaaag agaaatctag gctccaaggg     780
ggtgtcctgg tcaatgaaat cctcaatcac atgaagagag caactcagat accaagctac     840
aaaaaactta tcatgtattc tgcgcatgac actactgtga gtggcctaca gatggcgcta     900
gatgtttaca acggactcct tcctcctat gcttcttgcc acttgacgga attgtacttt     960
gagaaggggg agtactttgt ggagatgtac tatcggaatg acgcagca cgagccgtat    1020
cccctcatgc tacctggctg cagccctagc tgtcctctgg agaggtttgc tgagctggtt    1080
ggccctgtga tccctcaaga ctggtccacg gagtgtatga ccacaaacag ccatcaaggt    1140
actgaggaca gtacagatta g                                               1161
```

<210> SEQ ID NO 3
<211> LENGTH: 261
<212> TYPE: PRT
<213> ORGANISM: Homo sapiens

<400> SEQUENCE: 3

```
Met Trp Val Pro Val Phe Leu Thr Leu Ser Val Thr Trp Ile Gly
  1               5                  10                  15

Ala Ala Pro Leu Ile Leu Ser Arg Ile Val Gly Gly Trp Glu Cys Glu
                 20                  25                  30

Lys His Ser Gln Pro Trp Gln Val Leu Val Ala Ser Arg Gly Arg Ala
             35                  40                  45

Val Cys Gly Gly Val Leu Val His Pro Gln Trp Val Leu Thr Ala Ala
         50                  55                  60

His Cys Ile Arg Asn Lys Ser Val Ile Leu Leu Gly Arg His Ser Leu
     65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
```

```
                    145                 150                 155                 160
Glu Pro Glu Glu Phe Leu Thr Pro Lys Lys Leu Gln Cys Val Asp Leu
                165                 170                 175
His Val Ile Ser Asn Asp Val Cys Ala Gln Val His Pro Gln Lys Val
            180                 185                 190
Thr Lys Phe Met Leu Cys Ala Gly Arg Trp Thr Gly Gly Lys Ser Thr
        195                 200                 205
Cys Ser Gly Asp Ser Gly Gly Pro Leu Val Cys Asn Gly Val Leu Gln
    210                 215                 220
Gly Ile Thr Ser Trp Gly Ser Glu Pro Cys Ala Leu Pro Glu Arg Pro
225                 230                 235                 240
Ser Leu Tyr Thr Lys Val Val His Tyr Arg Lys Trp Ile Lys Asp Thr
                245                 250                 255
Ile Val Ala Asn Pro
                260

<210> SEQ ID NO 4
<211> LENGTH: 386
<212> TYPE: PRT
<213> ORGANISM: Homo sapiens

<400> SEQUENCE: 4

Met Arg Ala Ala Pro Leu Leu Leu Ala Arg Ala Ala Ser Leu Ser Leu
1               5                   10                  15
Gly Phe Leu Phe Leu Leu Phe Phe Trp Leu Asp Arg Ser Val Leu Ala
            20                  25                  30
Lys Glu Leu Lys Phe Val Thr Leu Val Phe Arg His Gly Asp Arg Ser
        35                  40                  45
Pro Ile Asp Thr Phe Pro Thr Asp Pro Ile Lys Glu Ser Ser Trp Pro
    50                  55                  60
Gln Gly Phe Gly Gln Leu Thr Gln Leu Gly Met Glu Gln His Tyr Glu
65                  70                  75                  80
Leu Gly Glu Tyr Ile Arg Lys Arg Tyr Arg Lys Phe Leu Asn Glu Ser
                85                  90                  95
Tyr Lys His Glu Gln Val Tyr Ile Arg Ser Thr Asp Val Asp Arg Thr
            100                 105                 110
Leu Met Ser Ala Met Thr Asn Leu Ala Ala Leu Phe Pro Pro Glu Gly
        115                 120                 125
Val Ser Ile Trp Asn Pro Ile Leu Leu Trp Gln Pro Ile Pro Val His
    130                 135                 140
Thr Val Pro Leu Ser Glu Asp Gln Leu Leu Tyr Leu Pro Phe Arg Asn
145                 150                 155                 160
Cys Pro Arg Phe Gln Glu Leu Glu Ser Glu Thr Leu Lys Ser Glu Glu
                165                 170                 175
Phe Gln Lys Arg Leu His Pro Tyr Lys Asp Phe Ile Ala Thr Leu Gly
            180                 185                 190
Lys Leu Ser Gly Leu His Gly Gln Asp Leu Phe Gly Ile Trp Ser Lys
        195                 200                 205
Val Tyr Asp Pro Leu Tyr Cys Glu Ser Val His Asn Phe Thr Leu Pro
    210                 215                 220
Ser Trp Ala Thr Glu Asp Thr Met Thr Lys Leu Arg Glu Leu Ser Glu
225                 230                 235                 240
Leu Ser Leu Leu Ser Leu Tyr Gly Ile His Lys Gln Lys Glu Lys Ser
                245                 250                 255
```

```
Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Gly Thr Glu Asp Ser
    370                 375                 380

Thr Asp
385

<210> SEQ ID NO 5
<211> LENGTH: 30
<212> TYPE: DNA
<213> ORGANISM: Homo sapiens

<400> SEQUENCE: 5
gttttgaata aaatttttt ataataaatc                                    30

<210> SEQ ID NO 6
<211> LENGTH: 43
<212> TYPE: DNA
<213> ORGANISM: Homo sapiens

<400> SEQUENCE: 6
aaaaaattga aatttatt tttttttttg aatataaat aat                       43

<210> SEQ ID NO 7
<211> LENGTH: 750
<212> TYPE: PRT
<213> ORGANISM: Homo sapiens

<400> SEQUENCE: 7

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125
```

-continued

```
Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
```

```
                545                 550                 555                 560
Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 8
<211> LENGTH: 123
<212> TYPE: PRT
<213> ORGANISM: Homo sapiens

<400> SEQUENCE: 8

Met Lys Ala Val Leu Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
            20                  25                  30

Glu Asp Cys Leu Gln Val Glu Asn Cys Thr Gln Leu Gly Glu Gln Cys
        35                  40                  45

Trp Thr Ala Arg Ile Arg Ala Val Gly Leu Leu Thr Val Ile Ser Lys
    50                  55                  60

Gly Cys Ser Leu Asn Cys Val Asp Asp Ser Gln Asp Tyr Tyr Val Gly
65                  70                  75                  80

Lys Lys Asn Ile Thr Cys Cys Asp Thr Asp Leu Cys Asn Ala Ser Gly
                85                  90                  95

Ala His Ala Leu Gln Pro Ala Ala Ala Ile Leu Ala Leu Leu Pro Ala
            100                 105                 110

Leu Gly Leu Leu Leu Trp Gly Pro Gly Gln Leu
        115                 120

<210> SEQ ID NO 9
<211> LENGTH: 339
<212> TYPE: PRT
<213> ORGANISM: Homo sapiens

<400> SEQUENCE: 9

Met Glu Ser Arg Lys Asp Ile Thr Asn Gln Glu Glu Leu Trp Lys Met
```

```
                1               5                  10                 15
Lys Pro Arg Arg Asn Leu Glu Glu Asp Asp Tyr Leu His Lys Asp Thr
                    20                  25                  30

Gly Glu Thr Ser Met Leu Lys Arg Pro Val Leu Leu His Leu His Gln
                    35                  40                  45

Thr Ala His Ala Asp Glu Phe Asp Cys Pro Ser Glu Leu Gln His Thr
                    50                  55                  60

Gln Glu Leu Phe Pro Gln Trp His Leu Pro Ile Lys Ile Ala Ala Ile
65                      70                  75                  80

Ile Ala Ser Leu Thr Phe Leu Tyr Thr Leu Arg Glu Val Ile His
                        85                  90                  95

Pro Leu Ala Thr Ser His Gln Gln Tyr Phe Tyr Lys Ile Pro Ile Leu
                    100                 105                 110

Val Ile Asn Lys Val Leu Pro Met Val Ser Ile Thr Leu Leu Ala Leu
                    115                 120                 125

Val Tyr Leu Pro Gly Val Ile Ala Ala Ile Val Gln Leu His Asn Gly
                    130                 135                 140

Thr Lys Tyr Lys Lys Phe Pro His Trp Leu Asp Lys Trp Met Leu Thr
145                     150                 155                 160

Arg Lys Gln Phe Gly Leu Leu Ser Phe Phe Ala Val Leu His Ala
                        165                 170                 175

Ile Tyr Ser Leu Ser Tyr Pro Met Arg Arg Ser Tyr Arg Tyr Lys Leu
                    180                 185                 190

Leu Asn Trp Ala Tyr Gln Gln Val Gln Gln Asn Lys Glu Asp Ala Trp
                    195                 200                 205

Ile Glu His Asp Val Trp Arg Met Glu Ile Tyr Val Ser Leu Gly Ile
                    210                 215                 220

Val Gly Leu Ala Ile Leu Ala Leu Leu Ala Val Thr Ser Ile Pro Ser
225                     230                 235                 240

Val Ser Asp Ser Leu Thr Trp Arg Glu Phe His Tyr Ile Gln Ser Lys
                    245                 250                 255

Leu Gly Ile Val Ser Leu Leu Leu Gly Thr Ile His Ala Leu Ile Phe
                    260                 265                 270

Ala Trp Asn Lys Trp Ile Asp Ile Lys Gln Phe Val Trp Tyr Thr Pro
                    275                 280                 285

Pro Thr Phe Met Ile Ala Val Phe Leu Pro Ile Val Val Leu Ile Phe
                    290                 295                 300

Lys Ser Ile Leu Phe Leu Pro Cys Leu Arg Lys Lys Ile Leu Lys Ile
305                     310                 315                 320

Arg His Gly Trp Glu Asp Val Thr Lys Ile Asn Lys Thr Glu Ile Cys
                        325                 330                 335

Ser Gln Leu

<210> SEQ ID NO 10
<211> LENGTH: 177
<212> TYPE: PRT
<213> ORGANISM: Homo sapiens

<400> SEQUENCE: 10

Met Gln Arg Arg Leu Val Gln Gln Trp Ser Val Ala Val Phe Leu Leu
1               5                   10                  15

Ser Tyr Ala Val Pro Ser Cys Gly Arg Ser Val Glu Gly Leu Ser Arg
                    20                  25                  30

Arg Leu Lys Arg Ala Val Ser Glu His Gln Leu Leu His Asp Lys Gly
```

```
                  35                  40                  45
Lys Ser Ile Gln Asp Leu Arg Arg Phe Phe Leu His His Leu Ile
 50                  55                  60

Ala Glu Ile His Thr Ala Glu Ile Arg Ala Thr Ser Glu Val Ser Pro
 65                  70                  75                  80

Asn Ser Lys Pro Ser Pro Asn Thr Lys Asn His Pro Val Arg Phe Gly
                 85                  90                  95

Ser Asp Asp Glu Gly Arg Tyr Leu Thr Gln Glu Thr Asn Lys Val Glu
                100                 105                 110

Thr Tyr Lys Glu Gln Pro Leu Lys Thr Pro Gly Lys Lys Lys Gly
                115                 120                 125

Lys Pro Gly Lys Arg Lys Glu Gln Glu Lys Lys Arg Arg Thr Arg
130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Arg
                165                 170                 175

His

<210> SEQ ID NO 11
<211> LENGTH: 111
<212> TYPE: PRT
<213> ORGANISM: Homo sapiens

<400> SEQUENCE: 11

Met Lys Thr Asn Asp Thr Tyr Met Lys Phe Ser Trp Leu Thr Val Pro
 1               5                  10                  15

Glu Lys Ser Leu Asp Lys Glu His Arg Cys Ile Val Arg His Glu Asn
                20                  25                  30

Asn Lys Asn Gly Val Asp Gln Glu Ile Ile Phe Pro Pro Ile Lys Thr
                35                  40                  45

Asp Val Ile Thr Met Asp Pro Lys Asp Asn Cys Ser Lys Asp Ala Asn
 50                  55                  60

Asp Thr Leu Leu Leu Gln Leu Thr Asn Thr Ser Ala Tyr Tyr Met Tyr
 65                  70                  75                  80

Leu Leu Leu Leu Leu Lys Ser Val Val Tyr Phe Ala Ile Ile Thr Cys
                85                  90                  95

Cys Leu Leu Arg Arg Thr Ala Phe Cys Cys Asn Gly Glu Lys Ser
                100                 105                 110

<210> SEQ ID NO 12
<211> LENGTH: 9
<212> TYPE: PRT
<213> ORGANISM: Homo sapiens

<400> SEQUENCE: 12

Cys Leu Ala Ala Gly Ile Thr Tyr Val
 1               5

<210> SEQ ID NO 13
<211> LENGTH: 9
<212> TYPE: PRT
<213> ORGANISM: Homo sapiens

<400> SEQUENCE: 13

Ile Met Asn Asp Met Pro Ile Tyr Met
 1               5
```

```
<210> SEQ ID NO 14
<211> LENGTH: 9
<212> TYPE: PRT
<213> ORGANISM: Homo sapiens

<400> SEQUENCE: 14

Val Leu Ala Gly Val Gly Phe Phe Ile
1               5

<210> SEQ ID NO 15
<211> LENGTH: 9
<212> TYPE: PRT
<213> ORGANISM: Homo sapiens

<400> SEQUENCE: 15

Leu Thr Leu Gly Glu Phe Leu Lys Leu
1               5

<210> SEQ ID NO 16
<211> LENGTH: 9
<212> TYPE: PRT
<213> ORGANISM: Homo sapiens

<400> SEQUENCE: 16

Lys Leu Phe Gly Val Leu Arg Leu Lys
1               5

<210> SEQ ID NO 17
<211> LENGTH: 9
<212> TYPE: PRT
<213> ORGANISM: Homo sapiens

<400> SEQUENCE: 17

Val Val Leu Gly Val Val Phe Gly Ile
1               5

<210> SEQ ID NO 18
<211> LENGTH: 15
<212> TYPE: PRT
<213> ORGANISM: Homo sapiens

<400> SEQUENCE: 18

Ser Val Ser Glu Ser Asp Thr Ile Arg Ser Ile Ser Ile Ala Ser
1               5                   10                  15

<210> SEQ ID NO 19
<211> LENGTH: 15
<212> TYPE: PRT
<213> ORGANISM: Homo sapiens

<400> SEQUENCE: 19

Leu Leu Ala Asn Gly Arg Met Pro Thr Val Leu Gln Cys Val Asn
1               5                   10                  15

<210> SEQ ID NO 20
<211> LENGTH: 15
<212> TYPE: PRT
<213> ORGANISM: Homo sapiens

<400> SEQUENCE: 20

Arg Met Pro Thr Val Leu Gln Cys Val Asn Val Ser Val Val Ser
1               5                   10                  15

<210> SEQ ID NO 21
```

```
-continued

<211> LENGTH: 103
<212> TYPE: PRT
<213> ORGANISM: Homo sapiens

<400> SEQUENCE: 21

Met Ser Gly Arg Gly Lys Gly Gly Lys Gly Leu Gly Lys Gly Gly Ala
1               5                   10                  15

Lys Arg His Arg Lys Val Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Gly Leu Ile Tyr Glu Glu Thr Arg Gly Val Leu Lys Val Phe Leu Glu
    50                  55                  60

Asn Val Ile Arg Asp Ala Val Thr Tyr Thr Glu His Ala Lys Arg Lys
65                  70                  75                  80

Thr Val Thr Ala Met Asp Val Val Tyr Ala Leu Lys Arg Gln Gly Arg
                85                  90                  95

Thr Leu Tyr Gly Phe Gly Gly
            100

<210> SEQ ID NO 22
<211> LENGTH: 10
<212> TYPE: PRT
<213> ORGANISM: Homo sapiens

<400> SEQUENCE: 22

Thr Met Asn Gly Ser Lys Ser Pro Val Glx
1               5                   10
```

USE OF MVA TO TREAT PROSTATE CANCER

CROSS-REFERENCE TO RELATED APPLICATIONS

This application claims the benefit of provisional Application No. 60/960,893, filed Oct. 18, 2007.

FIELD OF THE INVENTION

The invention relates to the prophylaxis and treatment of cancers, particularly prostate cancer, using MVA viruses encoding tumor-associated antigens, particularly prostate-specific antigen (PSA) and prostatic acid phosphatase (PAP).

BACKGROUND OF THE INVENTION

Modified Vaccinia Ankara (MVA) virus is related to vaccinia virus, a member of the genera Orthopoxvirus, in the family of Poxviridae. MVA was generated by 516 serial passages on chicken embryo fibroblasts of the Ankara strain of vaccinia virus (CVA) (for review see Mayr, A., et al. Infection 3:6-14 (1975)). As a consequence of these long-term passages, the genome of the resulting MVA virus had about 31 kilobases of its genomic sequence deleted and, therefore, was described as highly host cell restricted for replication to avian cells (Meyer, H. et al., J. Gen. Virol. 72:1031-1038 (1991)). It was shown in a variety of animal models that the resulting MVA was significantly avirulent (Mayr, A. & Danner, K., Dev. Biol. Stand. 41:225-34 (1978)). Additionally, this MVA strain has been tested in clinical trials as a vaccine to immunize against the human smallpox disease (Mayr et al., Zbl. Bakt. Hyg. I, Abt. Org. B 167:375-390 (1987); Stickl et al., Dtsch. med. Wschr. 99:2386-2392 (1974)). These studies involved over 120,000 humans, including high-risk patients, and proved that, compared to vaccinia-based vaccines, MVA had diminished virulence or infectiousness, while it induced a good specific immune response. In the following decades, MVA was engineered for use as a viral vector for recombinant gene expression or as a recombinant vaccine (Sutter, G. et al., Vaccine 12:1032-40 (1994)).

Even though Mayr et al. demonstrated during the 1970s that MVA is highly attenuated and avirulent in humans and mammals, certain investigators have reported that MVA is not fully attenuated in mammalian and human cell lines since residual replication might occur in these cells. (Blanchard et al., J Gen Virol 79:1159-1167 (1998); Carroll & Moss, Virology 238:198-211 (1997); Altenberger, U.S. Pat. No. 5,185,146; Ambrosini et al., J Neurosci Res 55(5):569 (1999)). It is assumed that the results reported in these publications have been obtained with various known strains of MVA, since the viruses used essentially differ in their properties, particularly in their growth behavior in various cell lines. Such residual replication is undesirable for various reasons, including safety concerns in connection with use in humans.

Strains of MVA having enhanced safety profiles for the development of safer products, such as vaccines or pharmaceuticals, have been described. See U.S. Pat. Nos. 6,761,893 and 6,193,752. Such strains are capable of reproductive replication in non-human cells and cell lines, especially in chicken embryo fibroblasts (CEF), but are not capable of reproductive replication in certain human cell lines known to permit replication with known vaccinia strains. Those cell lines include a human keratinocyte cell line, HaCat (Boukamp et al. J Cell Biol 106(3):761-71 (1988)), a human cervix adenocarcinoma cell line, HeLa (ATCC No. CCL-2), a human embryo kidney cell line, 293 (ECACC No. 85120602), and a human bone osteosarcoma cell line, 143B (ECACC No. 91112502). Such viral strains are also not capable of reproductive replication in vivo, for example, in certain mouse strains, such as the transgenic mouse model AGR 129, which is severely immune-compromised and highly susceptible to a replicating virus. See U.S. Pat. No. 6,761,893. One such MVA strain and its derivatives and recombinants, referred to as "MVA-BN®," have been described. See U.S. Pat. Nos. 6,761,893 and 6,193,752.

MVA and MVA-BN® have each been engineered for use as a viral vector for recombinant gene expression or as a recombinant vaccine. See, e.g., Sutter, G. et al., Vaccine 12:1032-40 (1994), U.S. Pat. Nos. 6,761,893 and 6,193,752.

Cancer-related diseases are a leading cause of mortality and morbidity worldwide. For example, in the US alone, it is estimated that one in six men will suffer from prostate cancer. Moreover, autopsy studies show that a significant proportion of the male population is known to carry the disease, albeit at its earliest non-malignant stages, as early as by the age of 30. See, e.g., Taichman et al., JCI 117(9):2351-2361 (2007); Webster et al., J. Clin. Oncol. 23:8262-8269 (2005). Recent approaches to cancer immunotherapy have included vaccination with tumor-associated antigens. In certain instances, such approaches have included use of a delivery system to promote host immune responses to tumor-associated antigens. Such delivery systems have included recombinant viral vectors, as well as cell-based therapies. See, e.g., Harrop et al., Front. Biosci. 11:804-817 (2006); Arlen et al., Semin. Oncol. 32:549-555 (2005); Liu et al., Proc. Natl. Acad. Sci. USA 101 (suppl. 2):14567-14571 (2004). MVA has been used as a vaccine vehicle for the 5T4 oncofetal antigen in clinical trials in metastatic colorectal, metastatic renal and hormone-refractory prostate cancer patients. Amato, R J., Expert Opin. Biol. Ther. 7(9): 1463-1469 (2007).

Among the known tumor-associated antigens are prostate-specific antigen (PSA) and prostatic acid phosphatase (PAP). See, e.g., Taichman et al., JCI 117(9): 2351-2361 (2007); Webster et al., J. Clin. Oncol. 23:8262-8269 (2005). PSA is produced by the prostate and is found in an increased amount in the blood of men who have prostate cancer, benign prostatic hyperplasia, or infection or inflammation of the prostate. PSA has been identified as a target for cell-mediated immunotherapy approaches to cancer treatment. See, e.g., McNeel, D. G., Curr. Opin. Urol. 17:175-181 (2007); Nelson W. G., Curr. Opin. Urol. 17:157-167 (2007). PAP is an enzyme measured in the blood whose levels may be elevated in patients with prostate cancer which has invaded or metastasized elsewhere. PAP is not elevated unless the tumor has spread outside the anatomic prostatic capsule, either through localized invasion or distant metastasis. Therefore this prostate tumor antigen is being investigated as a target antigen in several human vaccine trials, some with evidence of clinical benefit. See, e.g., McNeel, D. G., Curr. Opin. Urol. 17:175-181 (2007); Waeckerle-Men et al., Cancer Immunol. Immunother. 66:811-821 (2006); Machlenkin et al. Cancer Immunol Immunother. 56(2):217-226 (2007).

PAP containing vaccines have been generated using recombinant vaccinia virus, purified PAP, DNA vaccines, and antigen-loaded dendritic cells. Valone et al., The Cancer Journal 7: Suppl 2:S53-61 (2001); Fong et al., J Immunol. 2001 Dec. 15;167(12):7150-6; Fong et al., J. Immunol. 159(7): 3113-7 (1997); Johnson et al., Vaccine 24(3):293-303 (2006); Johnson et al., Cancer Immunol Immunother. 56(6):885-95 (2007). In one study, no antibodies to PAP were detected when dendritic cells pulsed with PAP-GM-CSF were injected into rats. (Valone et al. at S55.). In another study, administration of recombinant vaccinia virus containing genes encoding rat PAP or human PAP did not generate a measurable antibody response to rat or human PAP. (Fong et al. (1997) at 3116-7.) In another study, PAP-specific IgG could be detected in the sera of animals immunized with hPAP protein as well as in animals that received vaccinia virus encoding human PAP vaccination followed by hPAP protein as a booster immunization, but not in animals immunized twice with vaccinia virus encoding human PAP. (Johnson et al. (2007) at 890.)

Active cancer immunotherapy relies on the induction of an immune response against tumor cells in cancer patients. The induction of both humoral and cellular components of adaptive immunity against a broad range of tumor-associated antigens (TAA) and the concomitant activation of components of innate immunity are essential for maximal efficacy of an active immunotherapy product. Specifically, Type 1 or Th1 adaptive immunity characterized by the induction of antigen-specific IFNγ-producing cytotoxic T-cells (CD8 T-cells) is believed to be important for anti-cancer immunotherapy.

Despite the recent advances in cancer treatment, prostate cancer remains the second leading cause of death among American cancer patients. Thus, therapeutic approaches that might better alleviate the disease by targeting multiple aspects of tumor growth and metastasis are needed.

Taxanes, such as paclitaxel and docetaxel, have been used as chemotherapies for cancer patients. See, e.g., Tannock et al., N. Engl. J. Med. 351:1502-1512 (2004). Chemotherapy with taxanes has been combined with different tumor vaccine treatments, resulting in a variety of results. See, Chu et al., J. Immunotherapy 29:367-380 (2006); Machiels et al., Cancer Res. 61:3689-3697 (2001); Prell et al., Cancer Immunol. Immunother. 55:1285-1293 (2006); Arlen et al., Clinical Breast Cancer 7:176-179 (2006); and Arlen et al., Clinical Cancer Res. 12:1260-1269 (2006). The combination of cancer vaccines with chemotherapies has been reviewed in Chong et al., Expert Opin. Phamacother. 6:1-8 (2005); Emens et al., Endocrine-Related Cancer 12:1-17 (2005); and McNeel, D. G., Curr. Opin. Urol. 17:175-181 (2007).

Based on the above, a need in the art exists for reagents and methods for cancer therapy.

BRIEF SUMMARY OF THE INVENTION

The invention encompasses methods, reagents, and kits for cancer prophylaxis and the treatment of cancer patients, both of primary tumors and also of cancer metastasis.

The invention encompasses a method for treating a human cancer patient comprising administering to the patient a recombinant MVA encoding a polypeptide comprising a human prostate-specific antigen (PSA) antigen and a polypeptide comprising a human prostatic acid phosphatase (PAP) antigen. In one embodiment, the MVA is MVA-BN. In one embodiment, the MVA virus comprises the nucleotide sequence of SEQ ID NO:1 and SEQ ID NO:2. In one embodiment, the PSA antigen and the PAP antigen are inserted in the MVA intergenic region 014L/015L. In certain embodiments, the cancer is prostate cancer or a prostate cancer metastasis.

In one embodiment, the recombinant MVA is administered prior to a tumoricidal dose of a taxane. In one embodiment, the recombinant MVA is administered at the same time as a tumoricidal dose of a taxane. In one embodiment, the recombinant MVA is administered after a tumoricidal dose of a taxane. In preferred embodiments, the taxane is docetaxel or paclitaxel.

The invention encompasses kits for the prophylaxis of prostate cancer comprising a recombinant MVA encoding a polypeptide comprising a human PSA antigen and a polypeptide comprising a human PAP antigen and instructions to administer the recombinant MVA prior to the detection of prostate cancer.

The invention encompasses kits for the treatment of prostate cancer comprising a recombinant MVA encoding a polypeptide comprising a human PSA antigen and a polypeptide comprising a human PAP antigen and instructions to administer the recombinant MVA to a prostate cancer patient.

The invention encompasses kits for treating a cancer patient comprising a recombinant MVA encoding a polypeptide comprising a human PSA antigen and a polypeptide comprising a human PAP antigen and instructions to administer the recombinant MVA prior to, at the same time as, or after treatment with a tumoricidal dose of a taxane.

The invention encompasses a recombinant MVA virus expressing a polypeptide comprising a human PAP antigen. In one embodiment, the MVA virus comprises SEQ ID NO:2. In one embodiment, the MVA is MVA-BN.

The invention encompasses a recombinant MVA virus expressing a polypeptide comprising a human PSA antigen and a polypeptide comprising a human PAP antigen. In one embodiment, the MVA virus comprises the nucleotide sequence of SEQ ID NO:1. In one embodiment, the MVA virus comprises the nucleotide sequence of SEQ ID NO:2. In one embodiment, the MVA is MVA-BN.

The invention encompasses an immunogenic composition comprising a recombinant MVA virus encoding a polypeptide comprising a human PAP antigen, wherein the immunogenic composition induces B-cell and T-cell immune responses against PAP when administered to a host.

The invention encompasses an immunogenic composition comprising a recombinant MVA virus encoding a polypeptide comprising a human PAP antigen, wherein the immunogenic composition induces antibodies against PAP when administered to a host. In one embodiment, the MVA virus comprises SEQ ID NO:2.

The invention encompasses an immunogenic composition comprising a recombinant MVA virus encoding a polypeptide comprising a human PSA antigen and a polypeptide comprising a human PAP antigen, wherein the immunogenic composition induces B-cell and T-cell immune responses against PSA and PAP when administered to a host.

DETAILED DESCRIPTION OF THE INVENTION

Figure 1:
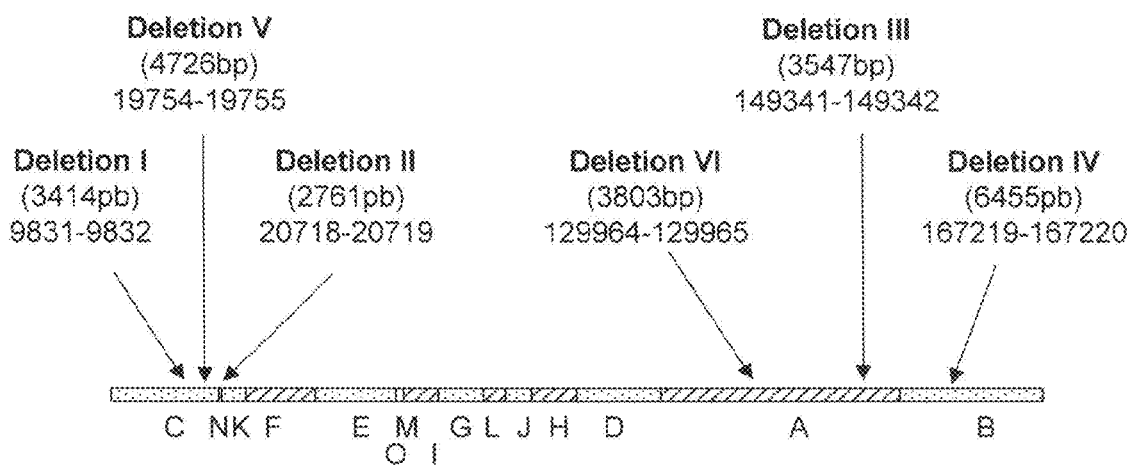
FIG. 1A-B. Schematic maps of MVA-BN® genome. Shown in 1A are the locations of the six deletion sites in the MVA-BN® genome: shaded sections and letters (A to O) identify HindIII restriction enzyme digestion fragments, and the positions and sizes of the CVA sequences that are lacking in the MVA-BN® are shown on the arrows. Shown in 1B are the HindIII restriction fragments (letters A to O) and the IGR 014L/015L site used to generation of MVA-BN-PRO.
Figure 1:
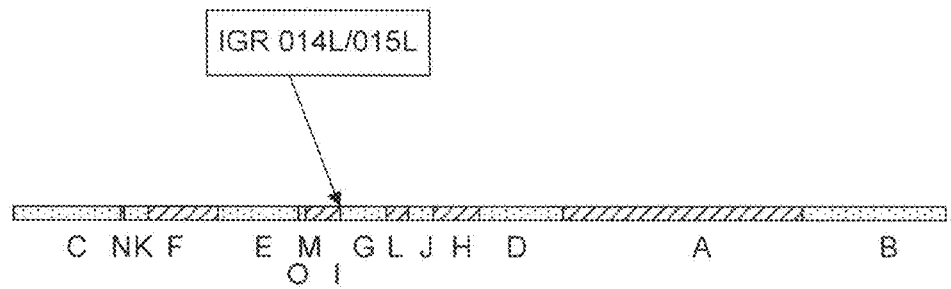

A recombinant MVA expressing human PSA and PAP antigens (MVA-BN-PRO) was tested in a panel of in vitro and in vivo assays. The expression of both prostate-specific antigens encoded by MVA-BN-PRO (PSA and PAP) in eukaryotic cells incubated with MVA-BN-PRO was evaluated using a PSA detection kit and a functional assay for phosphatase activity, respectively. ELISA and ELISpot assays were used to monitor the induction of anti-PSA and anti-PAP antibody and T-cell immune responses in mice treated with MVA-BN-PRO. The anti-tumor activity of MVA-BN-PRO was assessed in PSA-tumor models, both in a prophylactic setting and in a therapeutic setting.

These studies demonstrated that (i) uptake of MVA-BN-PRO by cells in vitro results in expression of both PAP and PSA in similar amounts; (ii) treatment of mice with MVA-BN-PRO results in anti-PSA and anti-PAP humoral and Th1 cellular immune responses, (iii) treatment of mice with MVA-BN-PRO inhibits the growth of PSA (+) tumors in both prophylactic and therapeutic settings, (iv) treatment of mice with MVA-BN-PRO inhibits the growth of PAP (+) tumors in a therapeutic setting, (v) in a human, MVA-BN-PRO treatment increased levels of both anti-PSA T cells and anti-PAP T cells, and (vi) MVA-BN-PRO treatment in a human resulted in the spreading of T cell responses to other tumor antigens. Thus, MVA-BN-PRO activates the immune system by triggering antigen-specific humoral and cellular Th1-type responses, which results in significant therapeutic activity against PSA and PAP expressing tumors in vivo. Consequently, MVA-BN-PRO is an attractive vaccine candidate for the immunotherapy of prostate cancer in humans.

MVA-BN-PRO is a potent immunogen able to induce protective anti-tumor immunity that prevents tumor growth in a prophylactic setting and that also suppresses the growth of established tumors. The prophylactic and therapeutic anti-tumor activities of MVA-BN-PRO were mediated by anti-PSA-specific adaptive immune responses. However, adaptive immune responses were induced against both prostate-specific antigens, PSA and PAP, encoded by MVA-BN-PRO. The concomitant activation of adaptive responses against multiple tumor antigens enables MVA-BN-PRO to combat tumors more efficiently and increase the potential to successfully treat cancer patients.

In one embodiment, the invention encompasses the use of recombinant MVA viruses for prostate cancer therapy. The recombinant MVAs are generated by insertion of heterologous sequences into an MVA virus. Examples of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom, with the deposition number ECACC 94012707 on Jan. 27, 1994, and MVA 575, deposited under ECACC 00120707 on Dec. 7, 2000. MVA-BN®, deposited on Aug. 30, 2000 at the European Collection of Cell Cultures (ECACC) under number V00083008, and its derivatives, are additional exemplary strains.

Although MVA-BN® is preferred for its higher safety (less replication competent), all MVAs are suitable for this invention. According to an embodiment of the present invention, the MVA strain is MVA-BN® and its derivatives. See PCT/EP01/13628, which is hereby incorporated by reference.

In certain embodiments, a recombinant MVA expresses a tumor-associated antigen. In one embodiment, tumor-associated antigen is PSA. In one embodiment, tumor-associated antigen is PAP. In a preferred embodiment, The MVA expresses two tumor-associated antigens, preferably a PSA and a PAP antigen. In one embodiment, the two tumor-associated antigens comprise the nucleotide sequences of SEQ ID NO:1 and SEQ ID NO:2. In one embodiment, the two tumor-associated antigens are expressed from a cassette comprising the nucleotide sequence of SEQ ID NO:3.

In further embodiments, the tumor-associated antigen is modified to include one or more foreign $T_H$ epitopes. As described herein, such cancer immunotherapeutic agents, are useful for the prophylaxis and/or treatment of cancer, including cancer metastasis. The invention allows for the use of such agents in prime/boost vaccination regimens of humans and other mammals, including immune-compromised patients; and inducing both humoral and cellular immune responses, such as inducing a Th1 immune response in a pre-existing Th2 environment.

The term "polypeptide" refers to a polymer of two or more amino acids joined to each other by peptide bonds or modified peptide bonds. The amino acids may be naturally occurring as well as non-naturally occurring, or a chemical analogue of a naturally occurring amino acid. The term also refers to proteins, i.e. functional biomolecules comprising at least one polypeptide; when comprising at least two polypeptides, these may form complexes, be covalently linked, or may be non-covalently linked. The polypeptide(s) in a protein can be glycosylated and/or lipidated and/or comprise prosthetic groups.

The term "not capable of reproductive replication" in human cell lines such as the cell lines HaCAT (Boukamp et al. 1988, J Cell Biol 106(3): 761-71) or HeLa is used in the present application as defined in WO 02/42480. Thus, a virus that is "not capable of reproductive replication" in a cell line is a virus that shows an amplification ratio of less than 1 in the cell line. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells. According to an embodiment of the present invention the viruses that are "not capable of reproductive replication" in human cell lines may have an amplification ratio of 1.0 (average value) or less, or even 0.8 (average value) or less, in any of the above human cell lines HeLa, HaCat and 143B.

In certain embodiments, the MVA is MVA-BN®, deposited on Aug. 30, 2000, at the European Collection of Cell Cultures (ECACC) under number V00083008, and described in U.S. Pat. Nos. 6,761,893 and 6,193,752. As described in those patent publications, MVA-BN® does not reproductively replicate in cell lines 293, 143B, HeLa and HaCat. In particular, MVA-BN® exhibits an amplification ratio of 0.05 to 0.2 in the human embryo kidney cell line 293. In the human bone osteosarcoma cell line 143B, MVA-BN® exhibits an amplification ratio of 0.0 to 0.6. MVA-BN® exhibits an amplification ratio of 0.04 to 0.8 in the human cervix adenocarcinoma cell line HeLa, and 0.02 to 0.8 in the human keratinocyte cell line HaCat. MVA-BN® has an amplification ratio of 0.01 to 0.06 in African green monkey kidney cells (CV1: ATCC No. CCL-70).

The amplification ratio of MVA-BN® is above 1 in chicken embryo fibroblasts (CEF: primary cultures) as described in U.S. Pat. Nos. 6,761,893 and 6,193,752. The virus can be easily propagated and amplified in CEF primary cultures with a ratio above 500.

In certain embodiments, a recombinant MVA is a derivative of MVA-BN®. Such "derivatives" include viruses exhibiting essentially the same replication characteristics as the deposited strain (ECACC No. V00083008), but exhibiting differences in one or more parts of its genome. The "derivatives" need not be derived from MVA-BN®. Viruses having the same "replication characteristics" as the deposited virus are viruses that replicate with similar amplification ratios as the deposited strain in CEF cells and the cell lines, HeLa, HaCat and 143B; and that show similar replication characteristics in vivo, as determined, for example, in the AGR129 transgenic mouse model.

The invention encompasses MVA viruses that have one or both of the following properties of MVA-BN:
 capability of reproductive replication in chicken embryo fibroblasts (CEF), but no capability of reproductive replication in the human keratinocyte cell line (HaCaT), the human embryo kidney cell line (293), the human bone osteosarcoma cell line (143B), and the human cervix adenocarcinoma cell line (HeLa); and
 failure to replicate in a mouse model that is capable of producing mature B and T cells and as such is severely immune compromised and highly susceptible to a replicating virus.

In certain embodiments, the MVA is a recombinant vaccinia virus that contains additional nucleotide sequences that are heterologous to the vaccinia virus. In certain such embodiments, the heterologous sequences code for epitopes that induce a response by the immune system. Thus, in certain embodiments, the recombinant MVA is used to vaccinate against the proteins or agents comprising the epitope. In a preferred embodiment, the epitope is a tumor-associated antigen, preferably, PSA or PAP. In one embodiment, the PSA antigen comprises the sequence of SEQ ID NO:1. In one embodiment, the PAP antigen comprises the sequence of SEQ ID NO:2.

In certain embodiments, a heterologous nucleic acid sequence is inserted into a non-essential region of the virus genome. In certain of those embodiments, the heterologous nucleic acid sequence is inserted at a naturally occurring deletion site of the MVA genome as described in PCT/EP96/02926. Methods for inserting heterologous sequences into the poxviral genome are known to a person skilled in the art. In certain embodiments, the heterologous nucleic acid sequence is inserted in an intergenic region of the MVA genome as described in published U.S. patent application 20050244428. In one embodiment, the intergenic region is IGR 014L/015L.

In certain embodiments, pharmaceutical compositions comprise one or more pharmaceutically acceptable and/or approved carriers, additives, antibiotics, preservatives, adjuvants, diluents and/or stabilizers. Such additives include, for example, but not limited to, water, saline, glycerol, ethanol, wetting or emulsifying agents, and pH buffering substances. Exemplary carriers are typically large, slowly metabolized molecules such as proteins, polysaccharides, polylactic acids, polyglycolic acids, polymeric amino acids, amino acid copolymers, lipid aggregates, or the like.

For the preparation of vaccines, the MVA can be converted into a physiologically acceptable form. In certain embodiments, such preparation is based on experience in the preparation of poxvirus vaccines used for vaccination against smallpox, as described, for example, in Stickl, H. et al., Dtsch. med. Wschr. 99:2386-2392 (1974).

An exemplary preparation follows. Purified virus is stored at −80° C. with a titer of $5 \times 10^8$ TCID$_{50}$/ml formulated in 10 mM Tris, 140 mM NaCl, pH 7.4. For the preparation of vaccine shots, e.g., $10^2$-$10^8$ particles of the virus can be lyophilized in phosphate-buffered saline (PBS) in the presence of 2% peptone and 1% human albumin in an ampoule, preferably a glass ampoule. Alternatively, the vaccine shots can be prepared by stepwise, freeze-drying of the virus in a formulation. In certain embodiments, the formulation contains additional additives such as mannitol, dextran, sugar, glycine, lactose, polyvinylpyrrolidone, or other additives, such as, including, but not limited to, antioxidants or inert gas, stabilizers or recombinant proteins (e.g. human serum albumin) suitable for in vivo administration. The ampoule is then sealed and can be stored at a suitable temperature, for example, between 4° C. and room temperature for several months. However, as long as no need exists, the ampoule is stored preferably at temperatures below −20° C.

In various embodiments involving vaccination or therapy, the lyophilisate is dissolved in 0.1 to 0.5 ml of an aqueous solution, preferably physiological saline or Tris buffer, and administered either systemically or locally, i.e., by parenteral, subcutaneous, intravenous, intramuscular, intranasal, intradermal, or any other path of administration known to a skilled practitioner. Optimization of the mode of administration, dose, and number of administrations is within the skill and knowledge of one skilled in the art.

In certain embodiments, attenuated vaccinia virus strains are useful to induce immune responses in immune-compromised animals, e.g., monkeys (CD4<400/µl of blood) infected with SIV, or immune-compromised humans. The term "immune-compromised" describes the status of the immune system of an individual that exhibits only incomplete immune responses or has a reduced efficiency in the defense against infectious agents.

Certain Exemplary Tumor-Associated Antigens

In certain embodiments, an immune response is produced in a subject against a cell-associated polypeptide antigen. In certain such embodiments, a cell-associated polypeptide antigen is a tumor-associated antigen.

In certain embodiments, a cell-associated polypeptide antigen is a self-protein antigen other than a tumor-associated antigen, which is related to various pathological processes, or a viral antigen, or antigens derived from an intracellular parasite or bacterium. In certain instances, such pathogen-associated antigens are often relatively poor immunogens (e.g. antigens from mycobacteria such as *Mycobacterium tuberculosis* and *Mycobacterium leprae*, but also from protozoans such as *Plasmodium* spp.).

Numerous tumor-associated antigens are known in the art. Exemplary tumor-associated antigens include, but are not limited to, 5alpha reductase, alpha-fetoprotein, AM-1, APC, April, BAGE, beta-catenin, Bcl12, bcr-abl, CA-125, CASP-8/FLICE, Cathepsins, CD19, CD20, CD21, CD23, CD22, CD33 CD35, CD44, CD45, CD46, CD5, CD52, CD55, C59, CDC27, CDK4, CEA, c-myc, Cox-2, DCC, DcR3, E6/E7, CGFR, EMBP, Dna78, farnesyl transferase, FGF8b, FGF8a, FLK-1/KDR, folic acid receptor, G250, GAGE-family, gastrin 17, gastrin-releasing hormone, GD2/GD3/GM2, GnRH, GnTV, GP1, gp100/Pmel17, gp-100-in4, gp15, gp75/TRP-1, hCG, heparanse, Her2/neu, HMTV, Hsp70, hTERT, IGFR1, IL-13R, iNOS, Ki67, KIAA0205, K-ras, H-ras, N-ras, KSA, LKLR-FUT, MAGE-family, mammaglobin, MAP17, melan-A/MART-1, mesothelin, MIC A/B, MT-MMPs, mucin, NY-ESO-1, osteonectin, p15, P170/MDR1, p53, p97/melanotransferrin, PAI-1, PDGF, uPA, PRAME, probasin, progenipoientin, PSA, PAP, PSM, RAGE-1, Rb, RCAS1, SART-1, SSX-family, STAT3, STn, TAG-72, TGF-alpha, TGF-beta, Thymosin-beta-15, TNF-alpha, TP1, TRP-2, tyrosinase, VEGF, ZAG, p16INK4, and glutathione-S-transferase. Particular examples of tumor-associated antigens in prostate cancer include, but are not limited to, PSA, prostate specific membrane antigen (PSMA), PAP, and prostate stem cell antigen (PSCA).

PSA and PAP Antigens

The invention encompasses PSA and PAP antigens that are full length or fragments of PSA and PAP. Preferably, the PSA and PAP antigens are human. In another embodiment, the PSA and/or PAP is rat or mouse. In a preferred embodiment, the PSA and PAP antigens are encoded by the nucleotide sequences of SEQ ID NO:1 and SEQ ID NO:2, respectively.

In one embodiment, the PAP antigen is a fragment of PAP. Preferred fragments comprise amino acids 181-95, 112-120, 133-152, 155-163, 173-192, 199-213, 228-242, 248-257, 299-307, or 308-322 of human PAP. See Waeckerle-Men et al., Cancer Immunol. Immunother. 55:1524-1533 (2006); Klyushnenkova et al., Prostate 67(10):1019-28 (2007); Matsueda et al., Clin Cancer Res. 11(19 Pt 1):6933-43 (2005); Harada et al., Oncol Rep. 12(3):601-7 (2004); Machlenkin et al., Cancer Res. 65(14):6435-6442 (2005); and McNeel et al., Cancer Res. 61(13):5161-7 (2001), which are hereby incorporated by reference. In one embodiment, the polypeptide comprises one of these epitopes. In other embodiments, the polypeptide comprises 2, 3, 4, 5, 6, 7, 8, 9, or 10 of these epitopes. Each of the possible combinations of these epitopes is specifically contemplated.

In certain embodiments, the fragment of PAP comprises 25, 50, 75, 100, 125, 150, 175, 200, 225, 250, 275, 300, 325, or 375 consecutive amino acids of human PAP. Fragments of PAP can be assayed for the retention of epitopes using well-known assays in the art. See, e.g., Klyushnenkova et al., Prostate 67(10):1019-28 (2007); Matsueda et al., Clin Cancer Res. 11(19 Pt 1):6933-43 (2005), which are hereby incorporated by reference.

DNAs encoding these fragments can be generated by PCR or other routine molecular biology techniques.

In one embodiment, the PSA antigen is a fragment of PSA. Preferred fragments comprise amino acids 16-24 or 154-163 of human PSA. See Waeckerle-Men et al., Cancer Immunol. Immunother. 55:1524-1533 (2006); Matsueda et al., Clin Cancer Res. 11(19 Pt 1):6933-43 (2005), which are hereby incorporated by reference. In one embodiment, the polypeptide comprises one of these epitopes. In other embodiments, the polypeptide comprises both of these epitopes.

Fragments of PSA can be assayed for the retention of epitopes using well-known assays in the art, such as epitope-scanning. In certain embodiment, the fragment of PSA comprises 25, 50, 75, 100, 125, 150, 175, 200, 225, or 250 consecutive amino acids of human PSA.

DNAs encoding these fragments can be generated by PCR or other routine molecular biology techniques.

Various modified PAP and PSA polypeptide antigens and methods can be produced by methods well-known in the art. For example, the methods described in U.S. Pat. No. 7,005,498 and U.S. Patent Pub. Nos. 2004/0141958 and 2006/0008465, which are hereby incorporated by reference, can be used.

The following parameters should be considered:
1. Known and predicted CTL epitopes;
2. Homology to related proteins;
3. Conservation of cysteine residues;
4. Predicted loop, a-helix and B-sheet structures;
5. Potential N-glycosylation sites;
6. Prediction of exposed and buried amino acid residues;
7. Domain organization.

Regions with a high degree of homology with other related proteins are likely to be structurally important for the "overall" tertiary structure, and hence for antibody recognition, whereas regions with low homology possibly can be exchanged with only local alterations of the structure as the consequence.

Cysteine residues are often involved in intramolecular disulphide bridge formation and are thus involved in the tertiary structure and should not be changed. Regions predicted to form alpha-helix or beta-sheet structures should be avoided as insertion points of foreign epitopes, as these regions are thought to be involved in folding of the protein.

Potential N-glycosylation sites should be conserved if mannosylation of the protein is desired.

Regions predicted (by their hydrophobic properties) to be interior in the molecule preferably should be conserved as these could be involved in the folding. In contrast, solvent exposed regions could serve as candidate positions for insertion of the model TH epitopes P2 and P30.

Finally, the domain organization of the protein should be taken into consideration because of its relevance for protein structure and function.

The effect of modifications of PSA and PAP can be assayed by immunizations of animals, such as mice, to determine the effect of the modifications on humoral and cellular immune responses.

Modified Tumor-Associated Antigens

In certain embodiments, a cell-associated polypeptide antigen is modified such that a CTL response is induced against a cell which presents epitopes derived from a polypeptide antigen on its surface, when presented in association with an MHC Class I molecule on the surface of an APC. In certain such embodiments, at least one first foreign $T_H$ epitope, when presented, is associated with an MHC Class II molecule on the surface of the APC. In certain such embodiments, a cell-associated antigen is a tumor-associated antigen.

Exemplary APCs capable of presenting epitopes include dendritic cells and macrophages. Additional exemplary APCs include any pino- or phagocytizing APC, which is capable of simultaneously presenting 1) CTL epitopes bound to MHC class I molecules and 2) $T_H$ epitopes bound to MHC class II molecules.

In certain embodiments, modifications to PSA and/or to PAP are made such that, after administration to a subject, polyclonal antibodies are elicited that predominantly react with PSA and/or to PAP. Such antibodies could attack and eliminate tumor cells as well as prevent metastatic cells from developing into metastases. The effector mechanism of this anti-tumor effect would be mediated via complement and antibody dependent cellular cytotoxicity. In addition, the induced antibodies could also inhibit cancer cell growth through inhibition of growth factor dependent oligo-dimerisation and internalisation of the receptors. In certain embodiments, such modified PSA and/or to PAP polypeptide antigens could induce CTL responses directed against known and/or predicted PSA and/or to PAP epitopes displayed by the tumor cells. In a preferred embodiment, the PSA and PAP antigens induce a B cell and a T cell response against these antigens.

In certain embodiments, a modified PSA and/or to PAP polypeptide antigen comprises a CTL epitope of the cell-associated polypeptide antigen and a variation, wherein the variation comprises at least one CTL epitope of a foreign $T_H$ epitope. Certain such modified PSA and/or to PAP polypeptide antigens comprising at least one CTL epitope and a variation comprising at least one CTL epitope of a foreign $T_H$ epitope, and methods of producing the same, are described in U.S. Pat. No. 7,005,498 and U.S. Patent Pub. Nos. 2004/0141958 and 2006/0008465.

In certain embodiments, a foreign $T_H$ epitope is a naturally-occurring "promiscuous" T-cell epitope. Such promiscuous T-cell epitopes are active in a large proportion of individuals of an animal species or an animal population. In certain embodiments, a vaccine comprises such promiscuous T-cell epitopes. In certain such embodiments, use of promiscuous T-cell epitopes reduces the need for a very large number of different CTL epitopes in the same vaccine. Exemplary promiscuous T-cell epitopes include, but are not limited to, epitopes from tetanus toxin, including but not limited to, the P2 and P30 epitopes (Panina-Bordignon et al., 1989), diphtheria toxin, Influenza virus hemagluttinin (HA), and P. falciparum CS antigen.

Additional promiscuous T-cell epitopes include peptides capable of binding a large proportion of HLA-DR molecules encoded by the different HLA-DR. See, e.g., WO 98/23635 (Frazer I H et al., assigned to The University of Queensland); Southwood S et. al, J. Immunol. 160:3363-3373 (1998); Sinigaglia F et al., Nature 336:778 780 (1988); Rammensee H G et al., Immunogenetics 41(4):178-228 (1995); Chicz R M et al., J. Exp. Med 178:27-47 (1993); Hammer J et al., Cell 74:197-203 (1993); and Falk K et al., Immunogenetics 39:230-242 (1994). The latter reference also deals with HLA-DQ and -DP ligands. All epitopes listed in these references are relevant as candidate natural epitopes as described herein, as are epitopes which share common motifs with these.

In certain other embodiments, the promiscuous T-cell epitope is an artificial T-cell epitope which is capable of binding a large proportion of haplotypes. In certain such embodiments, the artificial T-cell epitope is a pan DR epitope peptide ("PADRE") as described in WO 95/07707 and in the corresponding paper Alexander J et al., Immunity 1:751-761 (1994).

Recombinant MVA

The invention encompasses a recombinant MVA virus expressing a polypeptide comprising a PAP antigen. Preferably, MVA virus expresses a human PAP antigen. In one embodiment, the MVA virus expresses a rat or mouse PAP antigen. In one embodiment, MVA virus encodes a full length PAP antigen. In a preferred embodiment, the MVA comprises the nucleotide sequence of SEQ ID NO:2.

In another embodiment, the MVA encodes a fragment of a PAP. Fragments of PAP can be assayed for the retention of epitopes using well-known assays in the art. See, e.g., Klyushnenkova et al., Prostate 67(10):1019-28 (2007); Matsueda et al., Clin Cancer Res. 11(19 Pt 1):6933-43 (2005); Machlenkin et al., Cancer Res. 65(14):6435-6442 (2005), which are hereby incorporated by reference. In certain embodiment, the fragment of PAP comprises 25, 50, 75, 100, 125, 150, 175, 200, 225, 250, 275, 300, 325, or 375 consecutive amino acids of human PAP.

In preferred embodiments, the MVA encodes a polypeptide comprising amino acids 81-95, 112-120, 133-152, 155-163, 173-192, 199-213, 228-242, 248-257, 299-307, or 308-322 of human PAP. See Waeckerle-Men et al., Cancer Immunol. Immunother. 55:1524-1533 (2006); Klyushnenkova et al., Prostate 67(10):1019-28 (2007); Matsueda et al., Clin Cancer Res. 11(19 Pt 1):6933-43 (2005); Harada et al., Oncol Rep. 12(3):601-7 (2004); Machlenkin et al., Cancer Res. 65(14): 6435-6442 (2005); and McNeel et al., Cancer Res. 61(13): 5161-7 (2001), which are hereby incorporated by reference. In one embodiment, the polypeptide comprises one of these epitopes. In other embodiments, the polypeptide comprises 2, 3, 4, 5, 6, 7, 8, 9, or 10 of these epitopes. Each of the possible combinations of these epitopes is specifically contemplated.

The invention encompasses a recombinant MVA virus expressing a polypeptide comprising a PSA antigen and a recombinant MVA virus expressing a polypeptide comprising a PSA antigen and a polypeptide comprising a PAP antigen. Preferably, MVA virus expresses a human PSA antigen. In one embodiment, the MVA virus expresses a rat or mouse PSA antigen. In one embodiment, MVA virus encodes a full length PSA antigen. In a preferred embodiment, the MVA comprises the nucleotide sequence of SEQ ID NO:1.

In another embodiment, the MVA encodes a fragment of a PSA. Fragments of PSA can be assayed for the retention of epitopes using well-known assays in the art. In certain embodiment, the fragment of PSA comprises 25, 50, 75, 100, 125, 150, 175, 200, 225, or 250 consecutive amino acids of human PSA.

In preferred embodiments, the MVA encodes a polypeptide comprising amino acids 16-24 or 154-163 of human PSA. See Waeckerle-Men et al., Cancer Immunol. Immunother. 55:1524-1533 (2006); Matsueda et al., Clin Cancer Res. 11(19 Pt 1):6933-43 (2005), which are hereby incorporated by reference. In one embodiment, the polypeptide comprises one of these epitopes. In other embodiments, the polypeptide comprises both of these epitopes.

The recombinant MVA virus can be used in an immunogenic composition to induce B-cell and T-cell immune responses against PAP and/or PSA when administered to a host. In a preferred embodiment, the immunogenic composition induces antibodies against PAP and/or PSA when administered to a host. The immunogenic composition can contain adjuvants, diluents and/or stabilizers. Such additives include, for example, but not limited to, water, saline, glycerol, ethanol, wetting or emulsifying agents, and pH buffering substances.

In one embodiment, the MVA is MVA-BN®.

In a non-limiting embodiment, recombinant MVA comprising a tumor-associated antigen, e.g., MVA-BN-PRO, encoding both PSA and PAP antigens is constructed as follows. The initial virus stock is generated by recombination in cell culture using a cell type permissive for replication, e.g., CEF cells. Cells are both inoculated with an attenuated vaccinia virus, e.g., MVA-BN®, and transfected with a recombination plasmid (e.g., pBN217) that encodes the tumor-associated antigen, e.g., PSA or PAP, sequence and flanking regions of the virus genome. In one non-limiting embodiment, the plasmid pBN217 contains sequences which are also present in MVA-BN® (the 014L and 015L open reading frames). The PSA and PAP cDNA sequences are inserted between the MVA-BN® sequences to allow for recombination into the MVA-BN® viral genome. In certain embodiments, the plasmid also contains a selection cassette comprising one or more selection genes to allow for selection of recombinant constructs in CEF cells.

Simultaneous infection and transfection of cultures allows homologous recombination to occur between the viral genome and the recombination plasmid. Insert-carrying virus is then isolated, characterized, and virus stocks prepared. In certain embodiments, virus is passaged in CEF cell cultures in the absence of selection to allow for loss of the region encoding the selection genes, e.g., gpt and Red Fluorescent Protein (RFP).

Methods of Treatment

Patients with a cancer mediated by cells over-expressing a tumor-associated antigens, such as PSA and/or PAP, can be treated with recombinant MVA encoding one or more such antigens. In a preferred embodiment, the MVA is MVA-BN®. In a particularly preferred embodiment, the MVA encodes a polypeptide comprising the nucleotide sequence of SEQ ID NO:1 and a second polypeptide comprising the nucleotide sequence of SEQ ID NO:2.

The cancer is preferably a prostate cancer. In an embodiment, the cancer is metastatic prostate cancer. The cancer patient can be any mammal, including a mouse or rat. Preferably, the cancer patient is a primate, most preferably, a human.

The recombinant MVA encoding one or more tumor-associated antigens (e.g., PSA or PAP) can be administered either systemically or locally, i.e., by parenteral, subcutaneous, intravenous, intramuscular, intranasal, intradermal, or any other path of administration known to a skilled practitioner.

In one embodiment, $10^5$-$10^{10}$ TCID$_{50}$ of the recombinant MVA are administered to the patient. Preferably, $10^7$-$10^{10}$ TCID$_{50}$ of the recombinant MVA are administered to the patient. More preferably, $10^8$-$10^{10}$ TCID$_{50}$ of the recombinant MVA are administered to the patient. Most preferably, $10^8$-$10^9$ or $10^9$-$10^{10}$ TCID$_{50}$ of the recombinant MVA are administered to the patient. Preferably, the recombinant MVA are administered to the patient at a dose of $1\times10^8$, $2\times10^8$, or $4\times10^8$ TCID$_{50}$.

The recombinant MVA can be administered once, or at multiple times. In certain embodiments, the recombinant MVA is administered two, three, four, or five times. Preferably, the recombinant MVA is given three times. Most preferably, given three times at four-week intervals. The spacing between administrations is preferably 1-4 weeks, 1-8 weeks, 1-16 weeks, and 1-52 weeks. In one embodiment, the recombinant MVA is administered at day 0 and again at days 8 and 15. In a preferred embodiment, the dosage is escalated for subsequent administrations.

In a particularly preferred embodiment, $1\times10^8$, $2\times10^8$, and $4\times10^8$ $TCID_{50}$ are given three times at four-week intervals. The rationale for giving multiple doses of the recombinant MVA is based on preclinical immunogenicity data in mice showing that booster treatments significantly increased the anti-PSA and anti-PAP immune responses. Considering the vast immunological polymorphism in humans, giving three or more doses can ensure that every individual can reach maximal immune response.

In one embodiment, anti-PSA and/or anti-PAP antibody responses. In one embodiment, the treatment with the recombinant MVA induces anti-PSA and/or anti-PAP T-cell immune responses. In one embodiment, the treatment with the recombinant MVA induces anti-PSA and/or anti-PAP antibody and T-cell immune responses.

In one embodiment, the treatment with the recombinant MVA induces the spreading of T cell responses to other tumor antigens.

In one embodiment, the treatment with the recombinant MVA inhibits the growth of PSA (+) tumors in a prophylactic and/or therapeutic setting. In one embodiment, the treatment with the recombinant MVA inhibits the growth of PAP (+) tumors in a in a prophylactic and/or therapeutic setting. In one embodiment, the treatment with the recombinant MVA inhibits the growth of PSA (+) and PAP (+) tumors in a prophylactic and/or therapeutic setting.

Combination Therapy with Cytotoxic Agents

Patients with a cancer mediated by cells over-expressing a tumor-associated antigens, such as PSA and/or PAP, can be treated by the combination of a recombinant MVA encoding one or more such antigens with a taxane. Cytotoxic agents display immunomodulatory activities at sub-tumoricidal doses that could be beneficial for vaccine efficacy. At tumoricidal doses (high doses), use of these agents concurrently, prior to, or subsequent to treatment with the recombinant MVA can be superior to either treatment alone.

In one embodiment, the taxane is docetaxel. In another embodiment, the taxane is paclitaxel. The taxane is preferably administered at a tumoricidal dose. A "tumoricidal dose" of docetaxel is at least 50 mg/m$^2$. Preferably, the tumoricidal dose of docetaxel is 75-100 mg/m$^2$, which corresponds to a dosage of approximately 25-33 mg/kg. A "tumoricidal dose" of paclitaxel is at least 90 mg/m$^2$. Preferably, the tumoricidal dose of paclitaxel is 135-175 mg/m$^2$. A "sub-tumoricidal dose" of a taxane is a dosage below the tumoricidal dosage. The taxane can be administered by any means known to the skilled artisan, for example, intravenously.

In one embodiment, the taxane and the MVA encoding a polypeptide comprising a prostate tumor specific antigen are administered at the same time.

In one embodiment, the taxane is administered prior to the recombinant MVA. In one embodiment, the recombinant MVA is administered within 6 months of the taxane administration. In certain embodiments, the recombinant MVA is administered within 3 months, within 2 months, or within 1 month after the taxane. In one embodiment, the recombinant MVA is administered within 21 days after the taxane. In one embodiment, the recombinant MVA is administered within 14 days after the taxane. In one embodiment, the recombinant MVA is administered within 7 days after the taxane. Usually, the recombinant MVA is administered at least 2 days after treatment with the taxane.

In one embodiment, the taxane is administered after the recombinant MVA. Usually, the recombinant MVA is administered at least 1 week prior to treatment with the taxane. In one embodiment, the recombinant MVA is administered less than 2 years prior to the taxane. In certain embodiments, the recombinant MVA is administered less than 1 year, less than 6 months, or less than 3 months prior to the taxane. In one embodiment, the recombinant MVA is administered 1-26 weeks prior to the taxane. In one embodiment, the recombinant MVA is administered 1-9 weeks prior to the taxane. In one embodiment, the recombinant MVA is administered 1-3 weeks prior to the taxane.

In certain embodiments, the taxane is administered both prior to and after the recombinant MVA. In other embodiments, the recombinant MVA is administered both prior to and after the taxane. The administration of the recombinant MVA and the taxane can be a single administration or multiple administrations. For example, the administrations can be 1, 2, 3, 4, 5, or 6 weeks apart.

Kits

The invention encompasses kits comprising a recombinant MVA. The recombinant MVA may be contained in a vial or container. In one embodiment, the recombinant MVA encodes a PAP antigen. In one embodiment, the recombinant MVA encodes a polypeptide comprising a PSA antigen. In one embodiment, the recombinant MVA encodes a polypeptide comprising a PSA antigen and a polypeptide comprising a PAP antigen. In various embodiments, kits for vaccination comprising a recombinant MVA for the first vaccination ("priming") in a first vial or container and for a second or third vaccination ("boosting") in a second or third vial or container.

In one embodiment, the kit can contain a recombinant MVA and instructions for the administration of the recombinant MVA for the prophylaxis of prostate cancer. In one embodiment, the kit can contain a recombinant MVA and instructions for the administration of the recombinant MVA for the prophylaxis of prostate cancer after an increase in one or more prostate-tumor associated markers is detected. In a preferred embodiment, the instructions can instruct that the MVA is to be administered for the prophylaxis of prostate cancer after it is determined that the circulating PSA levels have increased. In one embodiment, the instructions can instruct that the MVA is to be administered for the prophylaxis of prostate cancer to a male patient after the age of 30 years old. In one embodiment, the instructions can instruct that the MVA is to be administered for the prophylaxis of prostate cancer to a male patient after the age of 30 years old and before the age of 40 years old. In one embodiment, the kit can contain a recombinant MVA and instructions for the administration of the recombinant MVA for the prophylaxis of prostate cancer after the age of 40.

In one embodiment, the kit can contain a recombinant MVA and instructions for the administration of the recombinant MVA for the prophylaxis of prostate cancer metastasis. In one embodiment, the kit can contain a recombinant MVA and instructions for the administration of the recombinant MVA for the prophylaxis of prostate cancer metastasis after an increase in a prostate tumor cell associated marker is detected. In a preferred embodiment, the instructions can instruct that the MVA is to be administered for the prophylaxis of prostate cancer metastasis after it is determined that the circulating PSA levels have increased, and despite the absence of a detectable primary tumor. In one embodiment, the instructions can instruct that the MVA is to be administered for the prophylaxis of prostate cancer metastasis to a male patient after the age of 30 years old. In one embodiment, the instructions can instruct that the MVA is to be administered for the prophylaxis of prostate cancer metastasis to a male patient after the age of 30 years old and before the age of 40 years old. In one embodiment, the kit can contain a recombinant MVA and instructions for the administration of the recombinant MVA for the prophylaxis of prostate cancer metastasis after the age of 40.

In one embodiment, the kit can contain a recombinant MVA and instructions for the administration of the recombinant MVA for the treatment of prostate cancer. In one embodiment, the kit can contain a recombinant MVA and instructions for the administration of the recombinant MVA for the treatment of prostate cancer after an increase in one or more prostate-tumor associated markers is detected. In a preferred embodiment, the instructions can instruct that the MVA is to be administered for the treatment of prostate cancer after it is determined that the circulating PSA levels have increased. In one embodiment, the instructions can instruct that the MVA is to be administered for the treatment of prostate cancer, to a male patient after the age of 30 years old. In one embodiment, the instructions can instruct that the MVA is to be administered for the treatment of prostate cancer, to a male patient after the age of 30 years old and before the age of 40 years old. In one embodiment, the kit can contain a recombinant MVA and instructions for the administration of the recombinant MVA for the treatment of prostate cancer after the age of 40.

In one embodiment, the kit can contain a recombinant MVA and instructions for the administration of the recombinant MVA prior to administration of a tumoricidal dose of a taxane. The instructions can instruct that the MVA is to be administered at any time point between 6 months and 1 week prior to taxane administration. In preferred embodiments, the instructions instruct that the MVA is to be administered at any time point between 3 months and 1 week, six weeks and 1 week, 1 month and 1 week, 3 weeks and 1 week, and 2 weeks and 1 week prior to taxane administration. In one embodiment, the instructions can instruct that the MVA is to be administered at any time point between 1 week and 0 days prior to taxane administration.

The kit can also contain a recombinant MVA and instructions for the administration of the recombinant MVA at the same time as administration of a tumoricidal dose of a taxane.

The kit can also contain a recombinant MVA and instructions for the administration of the recombinant MVA after administration of a tumoricidal dose of a taxane. The instructions can instruct that the MVA is to be administered at any time point between 1 day and 6 months after taxane administration. In preferred embodiments, the instructions instruct that MVA is to be administered at any time point between 2 days and 1 week, 2 days and 2 weeks, 2 days and 3 weeks, 2 days and 1 month, 2 days and 2 months, and 2 days and 3 months, and 2 days and 6 months after taxane administration. In one embodiment, the instructions can instruct that the MVA is to be administered at any time point between 0 and 2 days after taxane administration.

Examples and references are given below to illustrate the present invention in further detail, but the scope of the present invention is not limited by these examples. Any variations in the exemplified articles which occur to the skilled artisan are intended to fall within the scope of the present invention. Furthermore, the specification is most thoroughly understood in light of the cited references, all of which are hereby incorporated by reference in their entireties.

EXAMPLES

Example 1

Construction of MVA-BN-PRO and Analysis of Protein Expression in Infected Cells

To develop a prostate cancer vaccine, a recombinant vaccinia virus vector, MVA-BN-PRO, which encodes the human prostate specific antigen (PSA) and the prostate acidic phosphatase (PAP), was generated. The recombinant vaccinia virus vector MVA-BN-PRO was derived from the highly-attenuated vaccinia virus strain MVA-BN® (Modified Vaccinia Virus Ankara-Bavarian Nordic). MVA-BN® is strongly adapted to primary chicken embryo fibroblast (CEF) cells, and does not reproductively replicate in human cells. In human cells, viral genes are expressed, but no infectious virus is produced.

Origin of the Genes

The PSA gene and PAP cDNAs were transcribed (reverse transcription) from human prostate total RNA purchased from Clontech (Catalog # 6410801), using routine molecular biology techniques. PSA is a prostate specific antigen produced by the prostate and is found in an increased amount in the blood of men who have prostate cancer, benign prostatic hyperplasia, or infection or inflammation of the prostate. PSA has been identified as a target for cell-mediated immunotherapy approaches. PAP (Prostatic Acid Phosphatase) is an enzyme measured in the blood whose levels may be elevated in patients with prostate cancer which has invaded or metastasized elsewhere. PAP is not elevated unless the tumor has spread outside the anatomic prostatic capsule. Therefore this prostate tumor antigen is currently investigated as a target antigen in several human vaccine trials, some with evidence of clinical benefit.

The sequence of the resulting amplified PSA and PAP cDNAs were confirmed to match those published. That is, the PSA cDNA (e.g. among others GenBank M26663.1 GI:618463; synonyms: kallikrein 3; KLK3; 786 bp) and the sequence of the PAP cDNA gene (GenBank M34840.1 GI:189620; synonyms: PAP, ACP3, ACP-3; ACPP; 1161 bp) are shown below.

Human PSA cDNA sequence (99% identity to GenBank sequence M26663.1; bold: three silent nucleotide exchanges at position 48, 54 and 237, which do not change the amino acid sequence):

(SEQ ID NO: 1)
ATGTGGGTCCCGGTTGTCTTCCTCACCCTGTCCGTGACGTGGATTGGCGC

TGCGCCCCTCATCCTGTCTCGGATTGTGGGAGGCTGGGAGTGCGAGAAGC

ATTCCCAACCCTGGCAGGTGCTTGTGGCCTCTCGTGGCAGGGCAGTCTGC

GGCGGTGTTCTGGTGCACCCCAGTGGGTCCTCACAGCTGCCCACTGCAT

CAGGAACAAAAGCGTGATCTTGCTGGGTCGGCACAGTCTGTTTCATCCTG

AAGACACAGGCCAGGTATTTCAGGTCAGCCACAGCTTCCCACACCCGCTC

TACGATATGAGCCTCCTGAAGAATCGATTCCTCAGGCCAGGTGATGACTC

CAGCCACGACCTCATGCTGCTCCGCCTGTCAGAGCCTGCCGAGCTCACGG

ATGCTGTGAAGGTCATGGACCTGCCCACCCAGGAGCCAGCACTGGGGACC

ACCTGCTACGCCTCAGGCTGGGGCAGCATTGAACCAGAGGAGTTCTTGAC

-continued
CCCAAAGAAACTTCAGTGTGTGGACCTCCATGTTATTTCCAATGACGTGT

GTGCGCAAGTTCACCCTCAGAAGGTGACCAAGTTCATGCTGTGTGCTGGA

CGCTGGACAGGGGGCAAAAGCACCTGCTCGGGTGATTCTGGGGGCCCACT

TGTCTGTAATGGTGTGCTTCAAGGTATCACGTCATGGGGCAGTGAACCAT

GTGCCCTGCCCGAAAGGCCTTCCCTGTACACCAAGGTGGTGCATTACCGG

AAGTGGATCAAGGACACCATCGTGGCCAACCCCTGA

The amino acid sequence of human PSA is:

(SEQ ID NO: 3)
MWVPVVFLTLSVTWIGAAPLILSRIVGGWECEKHSQPWQVLVASRGRAVC

GGVLVHPQWVLTAAHCIRNKSVILLGRHSLFHPEDTGQVFQVSHSFPHPL

YDMSLLKNRFLRPGDDSSHDLMLLRLSEPAELTDAVKVMDLPTQEPALGT

TCYASGWGSIEPEEFLTPKKLQCVDLHVISNDVCAQVHPQKVTKFMLCAG

RWTGGKSTCSGDSGGPLVCNGVLQGITSWGSEPCALPERPSLYTKVVHYR

KWIKDTIVANP.

Human PAP cDNA sequence (100% identity to GenBank sequence M34840.1):

(SEQ ID NO: 2)
ATGAGAGCTGCACCCCTCCTCCTGGCCAGGGCAGCAAGCCTTAGCCTTGG

CTTCTTGTTTCTGCTTTTTTTCTGGCTAGACCGAAGTGTACTAGCCAAGG

AGTTGAAGTTTGTGACTTTGGTGTTTCGGCATGGAGACCGAAGTCCCATT

GACACCTTTCCCACTGACCCCATAAAGGAATCCTCATGGCCACAAGGATT

TGGCCAACTCACCCAGCTGGGCATGGAGCAGCATTATGAACTTGGAGAGT

ATATAAGAAAGAGATATAGAAAATTCTTGAATGAGTCCTATAAACATGAA

CAGGTTTATATTCGAAGCACAGACGTTGACCGGACTTTGATGAGTGCTAT

GACAAACCTGGCAGCCCTGTTTCCCCCAGAAGGTGTCAGCATCTGGAATC

CTATCCTACTCTGGCAGCCCATCCCGGTGCACACAGTTCCTCTTTCTGAA

GATCAGTTGCTATACCTGCCTTTCAGGAACTGCCCTCGTTTTCAAGAACT

TGAGAGTGAGACTTTGAAATCAGAGGAATTCCAGAAGAGGCTGCACCCTT

ATAAGGATTTTATAGCTACCTTGGGAAAACTTTCAGGATTACATGGCCAG

GACCTTTTTGGAATTTGGAGTAAAGTCTACGACCCTTTATATTGTGAGAG

TGTTCACAATTTCACTTTACCCTCCTGGGCCACTGAGGACACCATGACTA

AGTTGAGAGAATTGTCAGAATTGTCCCTCCTGTCCCTCTATGGAATTCAC

AAGCAGAAAGAGAAATCTAGGCTCCAAGGGGTGTCCTGGTCAATGAAAT

CCTCAATCACATGAAGAGAGCAACTCAGATACCAAGCTACAAAAAACTTA

TCATGTATTCTGCGCATGACACTACTGTGAGTGGCCTACAGATGGCGCTA

GATGTTTACAACGGACTCCTTCCTCCCTATGCTTCTTGCCACTTGACGGA

ATTGTACTTTGAGAAGGGGGAGTACTTTGTGGAGATGTACTATCGGAATG

AGACGCAGCACGAGCCGTATCCCCTCATGCTACCTGGCTGCAGCCCTAGC

TGTCCTCTGGAGAGGTTTGCTGAGCTGGTTGGCCCTGTGATCCCTCAAGA

-continued
CTGGTCCACGGAGTGTATGACCACAAACAGCCATCAAGGTACTGAGGACA

GTACAGATTAG

The amino acid sequence of human PAP is:

(SEQ ID NO: 4)
MRAAPLLLARAASLSLGFLFLLFFWLDRSVLAKELKFVTLVFRHGDRSPI

DTFPTDPIKESSWPQGFGQLTQLGMEQHYELGEYIRKRYRKFLNESYKHE

QVYIRSTDVDRTLMSAMTNLAALFPPEGVSIWNPILLWQPIPVHTVPLSE

DQLLYLPFRNCPRFQELESETLKSEEFQKRLHPYKDFIATLGKLSGLHGQ

DLFGIWSKVYDPLYCESVHNFTLPSWATEDTMTKLRELSELSLLSLYGIH

KQKEKSRLQGGVLVNEILNHMKRATQIPSYKKLIMYSAHDTTVSGLQMAL

DVYNGLLPPYASCHLTELYFEKGEYFVEMYYRNETQHEPYPLMLPGCSPS

CPLERFAELVGPVIPQDWSTECMTTNSHQGTEDSTD.

Origin of the Promoter

The A-type inclusion body promoter of cowpox virus (ATI), a late promoter (shown below), was synthetically generated in a pBluescript KS+ plasmid (Stratagene), excised and inserted in front of both the PAP sequence and the PSA sequence. Consequently, the PSA and PAP protein should be expressed with other late genes, after DNA replication.

Sequence of the ATI Promoter:

5'-GTTTTGAATAAAATTTTTTTATAATAAATC (SEQ ID NO: 5)

Construction of the PSA/PAP-MVA-BN Recombination Plasmid

For the insertion of foreign genes into the MVA-BN® genome, an intermediate recombination plasmid that targets a specific region of the MVA-BN® genome, namely a deletion site or an intergenic (non-coding) region, can be used.

The intermediate pBNX128 plasmid contains MVA DNA sequences from the regions that flank the intergenic (non-coding) region (IGR) between the 014L and 015L open reading frames (ORFs). Sequences, e.g. PSA and PAP cDNA, can be inserted between these flanking sequences. Then, when both plasmid and MVA-BN® are present in the same CEF cell, the 014L/015L flanking sequences mediate homologous recombination, mediating insertion of the plasmid sequences into the 014L/015L intergenic region of the MVA-BN® genome (FIG. 1A-B). The presence of a selection cassette in the inserted sequences allows for positive selection of recombinant MVA-BN® viruses.

Generation of MVA-BN-PRO

Simultaneous infection and transfection of cultures allowed homologous recombination to occur between the viral genome and the recombination plasmid. The resulting recombinant vaccinia vector, designated MVA-mBN106A, containing the PSA and PAP coding region and the selection cassette was obtained after multiple plaque purifications under selective conditions. After amplification and further plaque purification under non-selective conditions the recombinant vaccinia virus MVA-BN-PRO, devoid of the selection cassette, was isolated.

Plaque-purified virus MVA-BN-PRO lacking the selection cassette was prepared. Such preparation involved twelve (12) passages including four (4) plaque purifications.

Figure 2:
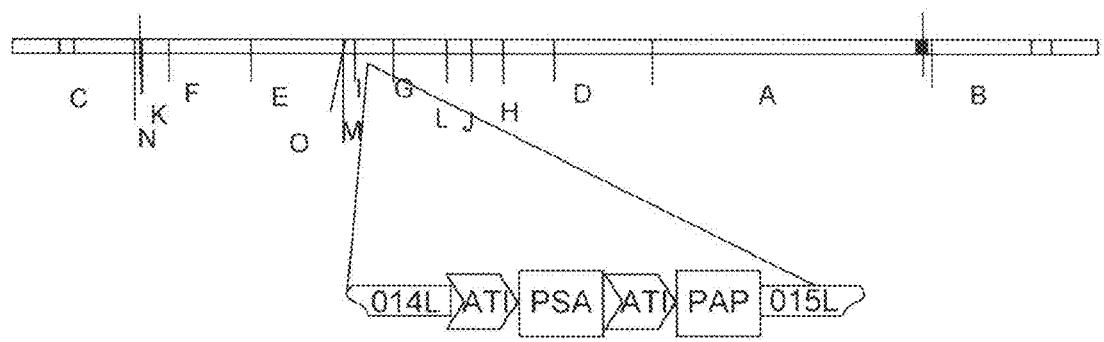
FIG. 2. Schematic Overview of the MVA-BN-PRO virus. Map of the MVA-BN® genome (HindIII restriction map, indicated by letters A to O) outlining the recombinant insert cloned in the intergenic region 014L/015L: PSA and PAP genes, each under the control of the cowpox virus ATI promoter (ATI).

The presence of the promoter-PSA-promoter-PAP sequence and absence of parental MVA-BN® virus in MVA-BN-PRO stocks was confirmed by DNA sequencing and PCR analysis, and nested PCR was used to verify the absence of the selection cassette (the gpt and RFP genes). A simplified schematic of the MVA-BN-PRO genome is shown in FIG. 2.

Example 2

PSA and PAP Co-expression in Cells Treated with MVA-BN-PRO

Simultaneous expression of the two prostate-specific antigens encoded by MVA-BN-PRO, namely human PSA and human PAP, was demonstrated in cells incubated with MVA-BN-PRO in vitro. Cultures of CT26, a chemically induced colorectal carcinoma of BALB/c mice (Brattain et al., Cancer Research 40, 2142-2146 (1980)), were incubated with MVA-BN-PRO and supernatants were analyzed for the presence of recombinant PSA and PAP. PSA was measured using an ELISA-based PSA diagnostic kit that is utilized routinely for the screening of human serum samples (Human PSA ELISA Kit, Anogen, Ontario, Canada; PSA detection range: 2-80 ng/mL). PAP was measured indirectly via its enzymatic properties using a calorimetric assay for phosphate activities (acidic phosphatase assay; PAP detection range: 4-40 ng/mL). PSA and PAP were assessed in aliquots of the same culture supernatants collected 24 hrs after adding MVA-BN-PRO at a multiplicity of infection (MOI) ranging from 1 to 100.

Figure 3:
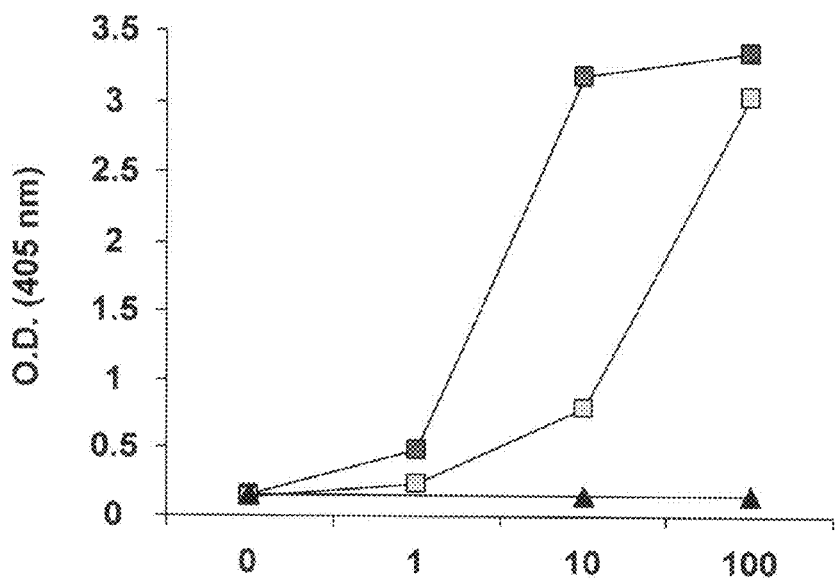
FIG. 3A-B. PAP (A) and PSA (B) detection in supernatant of CT26 cell cultures incubated with MVA-BN-PRO. CT26 cells at a density of $6 \times 10^5$ cells per well (dark squares and triangles) or 6E4 cells per well (grey squares) were infected with either MVA-BN-PRO (squares) or MVA-BN® (triangles) at indicated multiplicity of infection (MOI). 24 hours later, cell supernatants were harvested and PAP and PSA protein levels were measured by PAP enzymatic assay and PSA ELISA, respectively.
Figure 3:
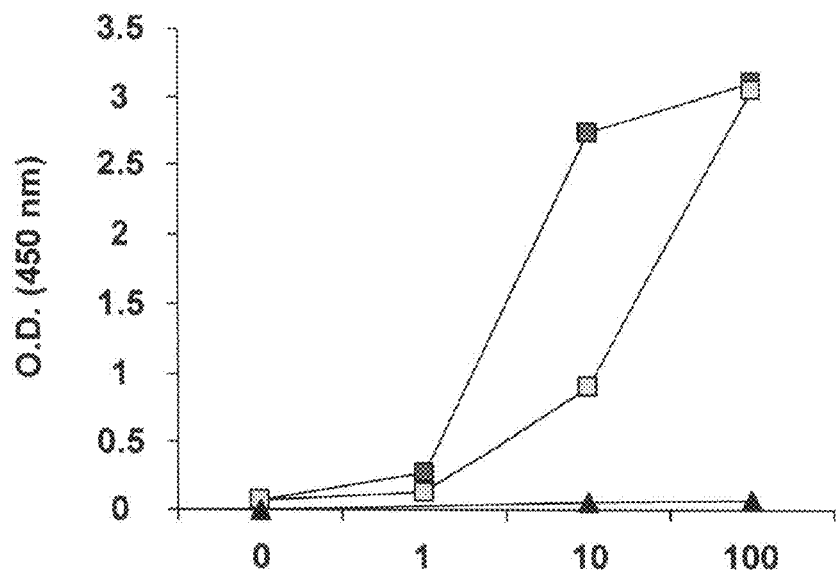

As shown FIG. 3, both antigens could be detected in the supernatants of cells incubated with MVA-BN-PRO. The amount of recombinant PSA and PAP produced in culture was dependent on the amount of MVA-BN-PRO (MOI) and the number of cells used in the experiment. In contrast, neither PSA nor phosphatase activity indicative of PAP could be detected in the supernatants of control cultures incubated either in media alone or with matching MOI of MVA-BN®.

The titration of PSA and PAP calculated using reference standard plots for each assay revealed that similar amounts of both antigens were produced by cells incubated with MVA-BN-PRO. Indeed, 1043 ng/mL PSA and 209 ng/mL PAP were measured in culture supernatants when CT26 were seeded at $1 \times 10^5$ cells per well and incubated with MVA-BN-PRO at an MOI of 10 for 48 hrs. PSA and PAP sequences are inserted in the same region of MVA-BN® genome and their expression is driven independently by an ATI promoter located upstream of each sequence. This insert configuration appears to confer the proper environment for optimal expression of both recombinant antigens. Overall, these data show that MVA-BN® represents an adequate delivery vehicle for a well-balanced and concomitant expression of multiple transgenic antigens like PSA and PAP.

Example 3

Induction of Anti-PAP and Anti-PSA Immune Response in Mice Treated with MVA-BN-PRO The induction of anti-PSA and anti-PAP immune responses upon treatment with MVA-BN-PRO was evaluated in BALB/c mice. In these studies, various doses of MVA-BN-PRO ranging from $2 \times 10^6$ to $5 \times 10^7$ TCID50 were evaluated. Blood samples were collected one day prior to each treatment and two weeks after the final treatment and humoral responses were analyzed by ELISA. Splenocytes were collected after the final treatment and cellular responses were analyzed by ELISpot.

Induction of Anti-PSA and Anti-PAP Antibody Responses

Figure 4:
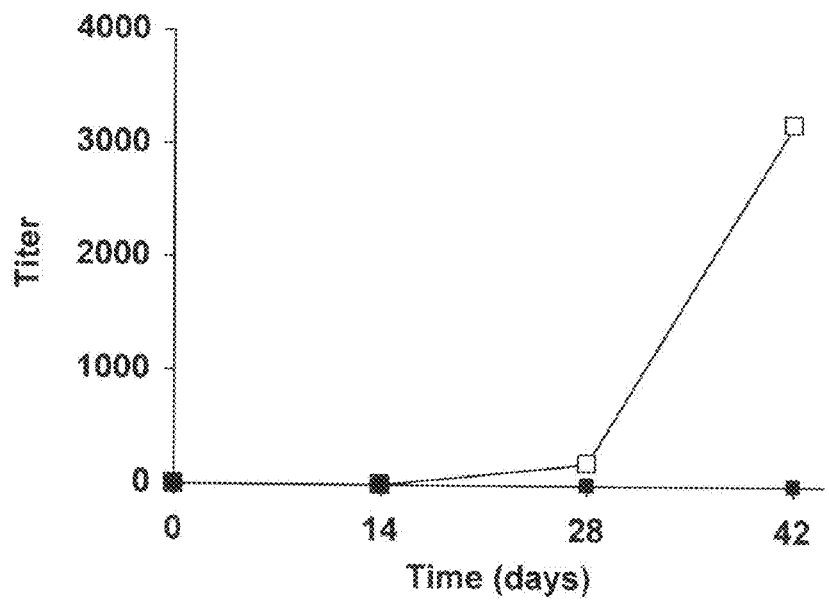
FIG. 4A-B. Anti-PSA (A) and Anti-PAP (B) Antibody Responses in Mice Treated with MVA-BN-PRO. Animals were immunized three times (day 1, 15, and 29) with either MVA-BN-PRO (white squares) or MVA-BN® (black squares). Blood samples were collected before treatment, at day 14, 28, and 42. Titers are the reciprocal value of the last dilution with an O.D. at least 2-fold higher than the background (serum at same dilution from TBS treated animals). Titers indicated as zero were negative at the lowest serum dilution tested (1:50).
Figure 4:
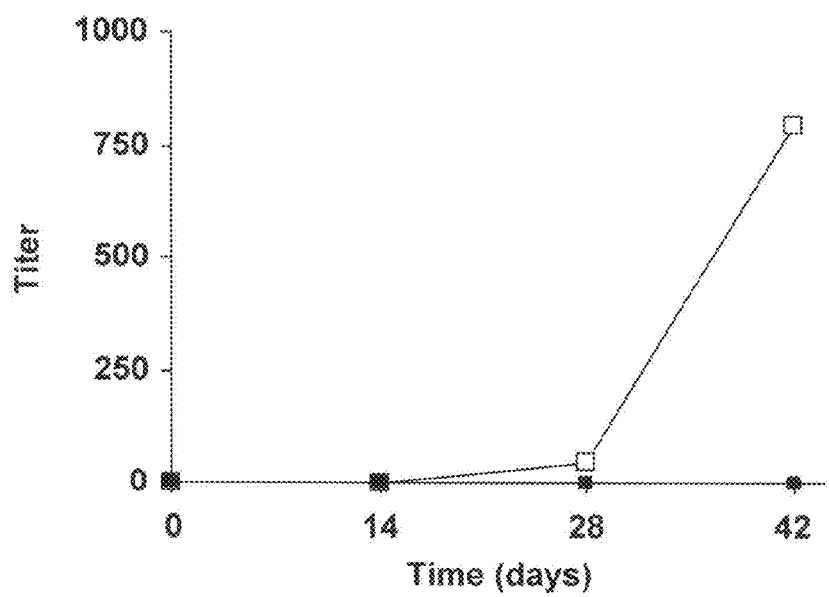

BALB/c mice (5 animals in each group) were treated subcutaneously with $5 \times 10^7$ TCID50 of MVA-BN-PRO at day 1, 15 and 29 (q2 weeks×3). Control animals were treated with MVA-BN® or formulation buffer (TBS). Blood samples were collected before treatment, at day 14, 28, and 42. Sera from mice of each test group were then pooled and analyzed by ELISA. The induction of anti-PSA and anti-PAP antibody responses was evaluated using commercially available purified proteins (Meridian Life Sciences, Inc., Saco, Me.) as target antigens coated onto the wells of a microtitration plate. As shown in FIGS. 4A and 4B, anti-PSA and anti-PAP antibody responses were detected in MVA-BN-PRO-treated mice. Detection of anti-PSA antibody titers required at least two administrations and titers increased following the third treatment with MVA-BN-PRO. Generally, the antibody response against PAP was more modest as titers were always lower than those induced against PSA. The low antibody response observed against PAP is likely due to the weak B-cell antigenic property of this protein.

Induction of Anti-PSA and Anti-PAP T-Cell Responses

Figure 5:
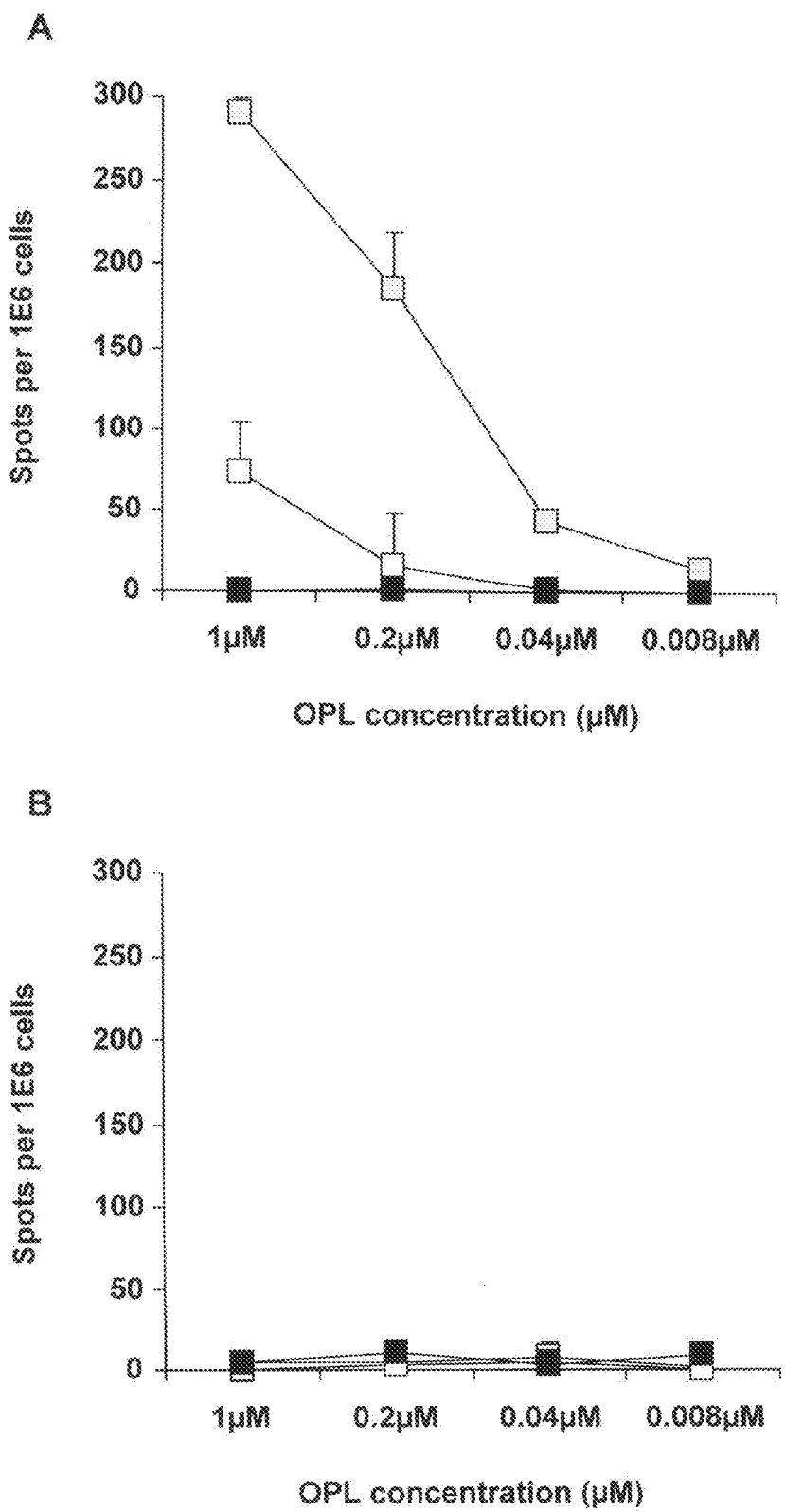
FIG. 5A-B. Anti-PSA and Anti-PAP T-cell Responses in Mice Treated with MVA-BN-PRO. Splenocytes from MVA-BN-PRO immunized animals (A) and TBS control animals (B) were incubated with OPL from PAP (gray squares), PSA (white squares) or HER2 (black squares) sequences at the indicated concentrations. Spots indicative of IFN-γ-producing T-cells were numerated using an ImmunoSpot Analyzer. Means from triplicate wells and standard deviation are represented for each OPL concentration tested.

BALB/c mice (5 animals in each group) were treated subcutaneously with either control (TBS), $2 \times 10^6$ or $5 \times 10^7$ TCID50 of MVA-BN-PRO on day 1, 15, 31 (q2w×3). Spleens were collected 5 days after the last immunization and cell suspensions from each test group were pooled for analysis. The induction of T-cell responses was evaluated by ELISpot that measured IFNγ production after in vitro antigen-specific restimulation. Libraries of 15-mer peptides with 11-mer overlaps (OPLs) and covering either the full-length of PSA or PAP amino acid sequences were used separately for restimulation. As shown in FIG. 5, antigen-specific T-cell responses were detected in spleen cells from the MVA-BN-PRO treatment group upon restimulation with both PAP and PSA OPLs, while a control OPL derived from human HER-2 ecd sequence had no effect (FIG. 5A). No T-cell responses were detected in mice of the MVA-BN® (data not shown) or TBS-treated groups (FIG. 5) when cells were restimulated with PSA, PAP or HER-2 OPLs. These data indicate that MVA-BN-PRO is a potent T-cell inducer since significant numbers of antigen-specific T-cell could be detected directly in splenocytes without ex vivo expansion.

Figure 6:
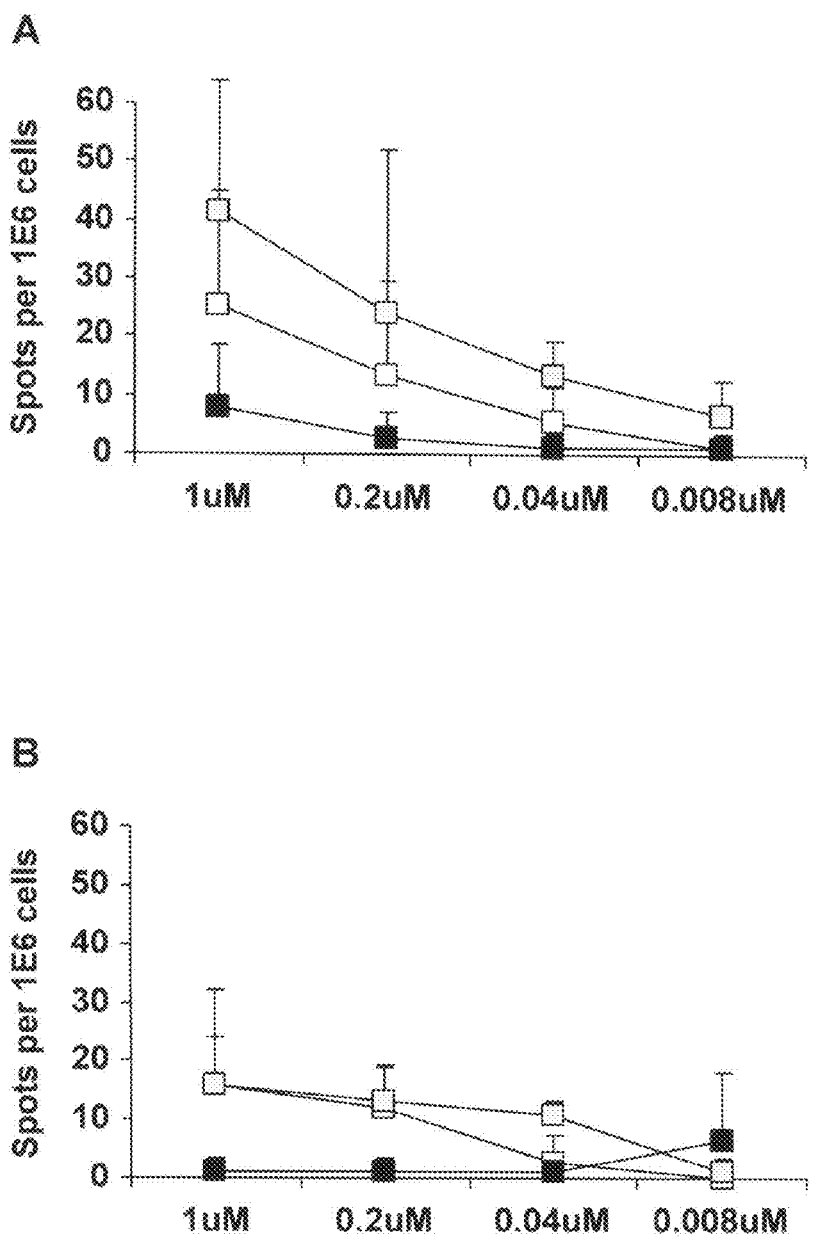
FIG. 6A-B. CD4 and CD8 T-cell Contributions to MVA-BN-PRO Mediated T-cell Responses. Animals were immunized with MVA-BN-PRO four times (d 1, 15, 29, and 49) and splenocytes were collected six days after the last treatment, CD8 depleted splenocytes (A) and CD4 depleted splenocytes (B) were incubated with OPL from PAP (gray squares), PSA (white squares) or HER2 (black squares) sequences at the indicated concentrations. The analysis was carried out as described for FIG. 5.

The contribution of CD4 helper and CD8 cytotoxic T-cells to the anti-PAP and PSA T-cell responses induced in mice upon treatment with MVA-BN-PRO was examined following depletion of T-cell subset populations prior to in vitro restimulation of spleen cells. As shown FIG. 6, T-cell responses were detected in both CD4- and CD8-depleted T-cell subsets upon restimulation with either PSA or PAP OPL.

Overall, these studies show that repeated treatment of mice with MVA-BN-PRO induces a broad antigen-specific adaptive immune response to two TAAs that involves antibody and both CD4 and CD8 effector cell subtypes. As expected, the antibody response was mainly directed toward PSA while PAP, a known weak B-cell immunogen, triggered only a modest antibody response. Because PSA and PAP are essentially represented on tumor cell surface as T-cell targets in the form of antigen-presenting molecule/peptide complexes, the activation of cellular components of the immune system is a critical requirement for MVA-BN-PRO potency. Strong CD4 and CD8 T-cell responses were induced against both TAAs in animals treated with all MVA-BN-PRO doses tested. Therefore, MVA-BN-PRO has the potential to mediate the elimination of tumor cells presenting PSA and/or PAP peptides on their surface.

Example 4

Anti-tumor Activity in Mice Treated with MVA-BN-PRO

The ability of MVA-BN-PRO to affect the growth of PSA-positive tumor cells in mice was evaluated in a prophylactic as well as a therapeutic cancer tumor model. The data show that MVA-BN-PRO can inhibit tumor growth in both settings. Also, MVA-BN-PRO was able to inhibit the growth of PAP-positive tumor cells in mice in a therapeutic cancer tumor model.

Induction of Protective Antigen-specific Adaptive Immunity Upon Treatment with MVA-BN-PRO (Prophylactic Setting)

The ability of MVA-BN-PRO to prevent tumor growth was evaluated using transplanted E5 cells as a prostate cancer model. E5 is a subclone of RM11, a murine prostate tumor cell line (Elzey et al., Int. J Cancer 15;94(6):842-9 (2001)) obtained after transfection of RM11 with recombinant DNA encoding the human PSA gene. In this efficacy study, mice where immunized with MVA-BN-PRO as described above, i.e., three times at 3-week intervals with either TBS, MVA-BN® ($5\times10^7$ $TCID_{50}$) or MVA-BN-PRO ($2\times10^6$, $1\times10^7$ or $5\times10^7$ $TCID_{50}$). Mice were then challenged with tumors by injecting $1\times10^5$ E5 cells intradermally six weeks after the last treatment. Tumor growth was observed twice weekly thereafter and the size of solid growing tumors was measured.

Figure 7:
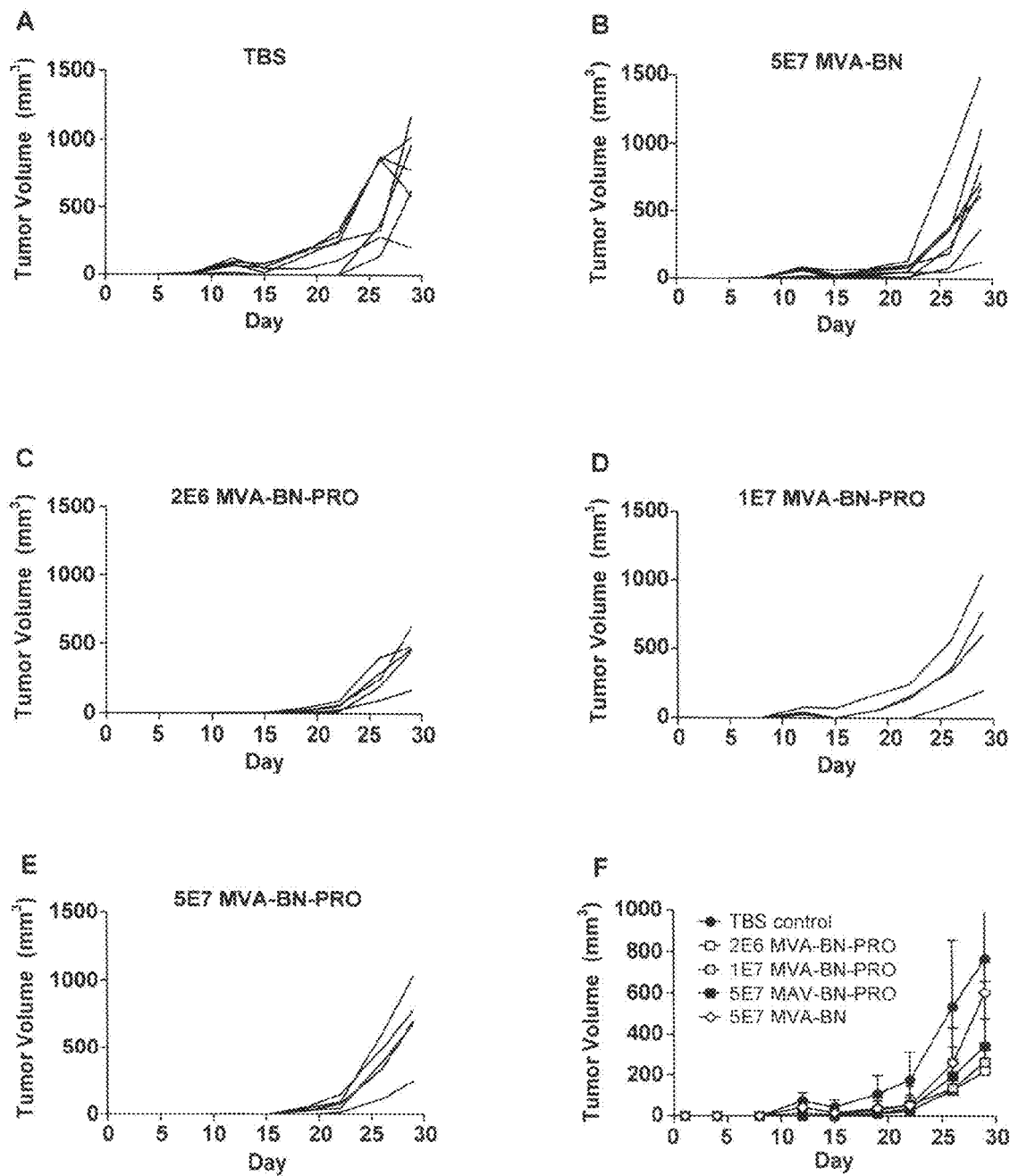
FIG. 7A-F. Prophylatic prevention of tumor growth in mice treated with MVA-BN-PRO. Animals were treated 3 times at 3 week intervals at indicated TCID50 of virus diluted in TBS. Six weeks after the third treatment animals were challenged intradermally with $1\times10^5$ PSA-expressing E5 tumor cells. Tumor growth was measured twice weekly using calipers. Tumor volume was calculated as: $(L\times W^2)/2$. 7A through 7E: tumor growth in individual mice is reported for each treatment group. 7F: mean tumor sizes and standard deviation are reported for all treatment groups.

As shown in FIGS. 7C to 7E, the tumors in animals pre-treated with all doses of MVA-BN-PRO grew slower than the tumors of the TBS control group (FIG. 7A), and >50% of the mice remained tumor-free for all the doses tested at the end of study (Day 29). In contrast, measurable tumors were detected in 100% of the mice in the TBS control groups as early as Day 12 post tumor challenge. On that day, measurable tumors were detected in only 20% of the mice from all MVA-BN-PRO treatment groups. The difference in mean tumor sizes was statistically significant between all MVA-BN-PRO treated groups and the TBS control group at all time points from Day 12 throughout the study (FIG. 7F).

Similarly to the TBS control group, measurable tumors were detected in almost every MVA-BN®-treated mouse (90%) as early as Day 12 post tumor challenge (FIG. 7B). However, 2 mice in the MVA-BN®-treated group (20%) were tumor-free at the end of study (Day 29; one mouse remained tumor-free throughout the study and tumor regression occurred in the other mouse). Also, tumors in the MVA-BN®-treated group grew slower than the tumors of the TBS control group until Day 22 and statistically significant differences in the mean tumor sizes between these two groups were reached at two time points (Day 19, p=0.034 and Day 22, p=0.019). The delay of tumor growth in MVA-BN®-treated mice was only transient since similar mean tumor sizes were observed in the TBS and MVA-BN®-treated mice at all other time points (FIG. 7F).

Figure 8:
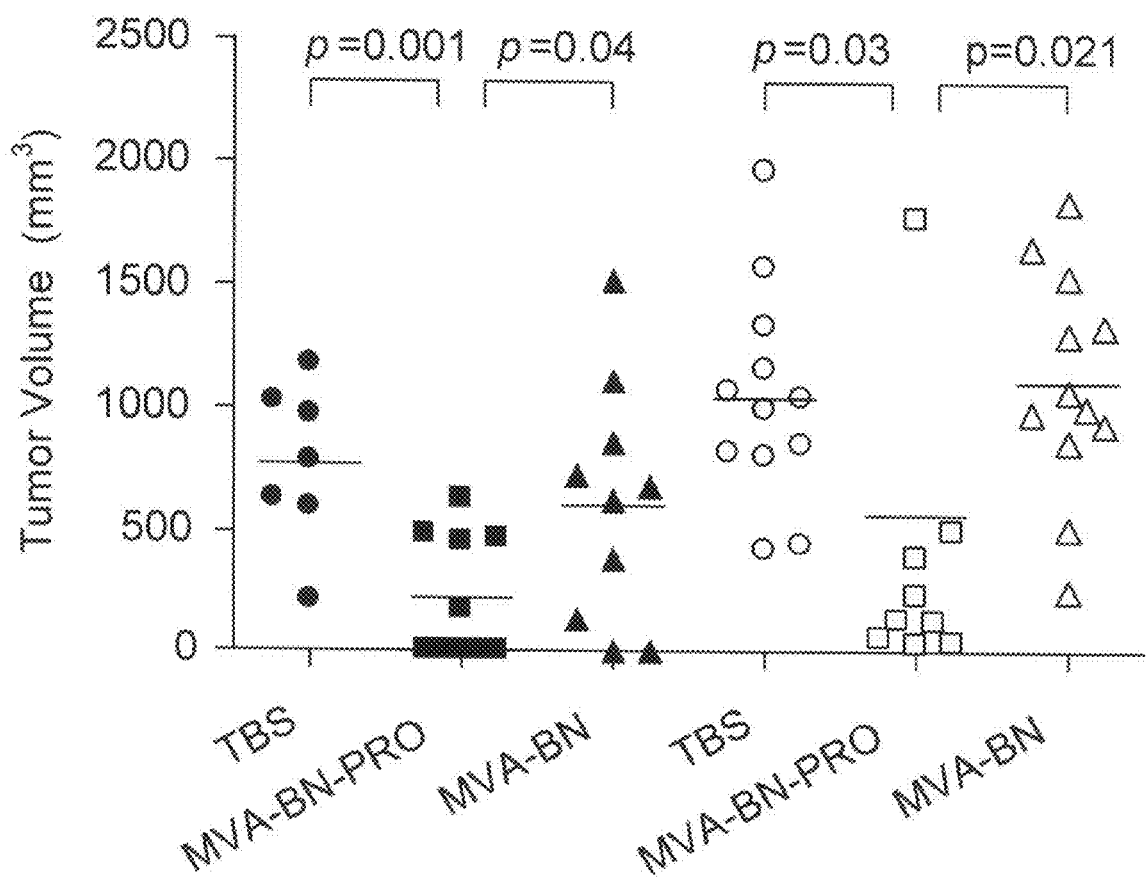
FIG. 8. Prevention of Tumor Growth in Mice Treated with MVA-BN-PRO. Comparison of Day 29 Measurements in two Separate Experiments. Animals were treated three times at 2-week intervals (grey symbols) with $2\times10^6$ TCID$_{50}$ of indicated virus diluted in TBS. Two weeks after the last treatment, animals were challenged intradermally with $1\times10^5$ PSA-expressing E5 tumor cells. Tumor growth was measured twice weekly using calipers. Tumor volume was calculated as: $(L\times W^2)/2$. Dots show tumor volumes for each animal on Day 29 post tumor implantation. Data from the matching groups of a separate experiment described in FIG. 7 are represented in black symbols for comparison. Both experiments reported here were conducted under similar conditions except for the length of treatment intervals (3-week vs 2-week intervals) and the time of tumor cell implantation (six vs. two weeks after the third treatment).

The MVA-BN-PRO-mediated anti-tumor activity described above was confirmed in a repeat experiment where mice were treated with $2\times10^6$ $TCID_{50}$ MVA-BN-PRO at 2-week intervals, then challenged with tumor cells two weeks post-treatment. The data at Day 29 post tumor implantation are shown FIG. 8, along the matching data from FIG. 7 for the same day post implantation. Comparable delay of tumor growth was observed in mice treated with MVA-BN-PRO in both experiments. Moreover, statistically significant differences in the mean tumor sizes were reached between MVA-BN-PRO- and TBS-treated groups as well as between MVA-BN-PRO- and MVA-BN-treated groups (p=0.03 and p=0.021, respectively). The transient effect of MVA-BN® observed at early time points in FIG. 7 was not detected in the repeat experiment (data not shown). These data show that treatment of mice with MVA-BN-PRO induces an antigen-specific adaptive immune response and the establishment of immune memory. When mice are subsequently challenged two to six weeks later with tumor cells, the immune memory is recalled and inhibits the growth of the tumor cells.

Suppression of Tumors upon Treatment with MVA-BN-PRO (Therapeutic Setting)

The ability of MVA-BN-PRO to suppress established tumors was evaluated using transplanted E6 cells as a prostate cancer model. E6 is a subclone of RM11, a murine prostate tumor cell line (Elzey et al., 2001) obtained after transfection RM11 with recombinant DNA encoding the human PSA gene. E6 is a lower producer of PSA than E5, which was used in the prophylactic setting described above. Mice were challenged with tumors by injecting $1\times10^5$ E6 cells intradermally and treated on the same day, then on Day 8 and 15 with either TBS, MVA-BN® or MVA-BN-PRO ($5\times10^6$ or $5\times10^7$ $TCID_{50}$). Tumor growth was observed twice weekly thereafter and the size of solid tumors under the skin was measured.

Figure 9:
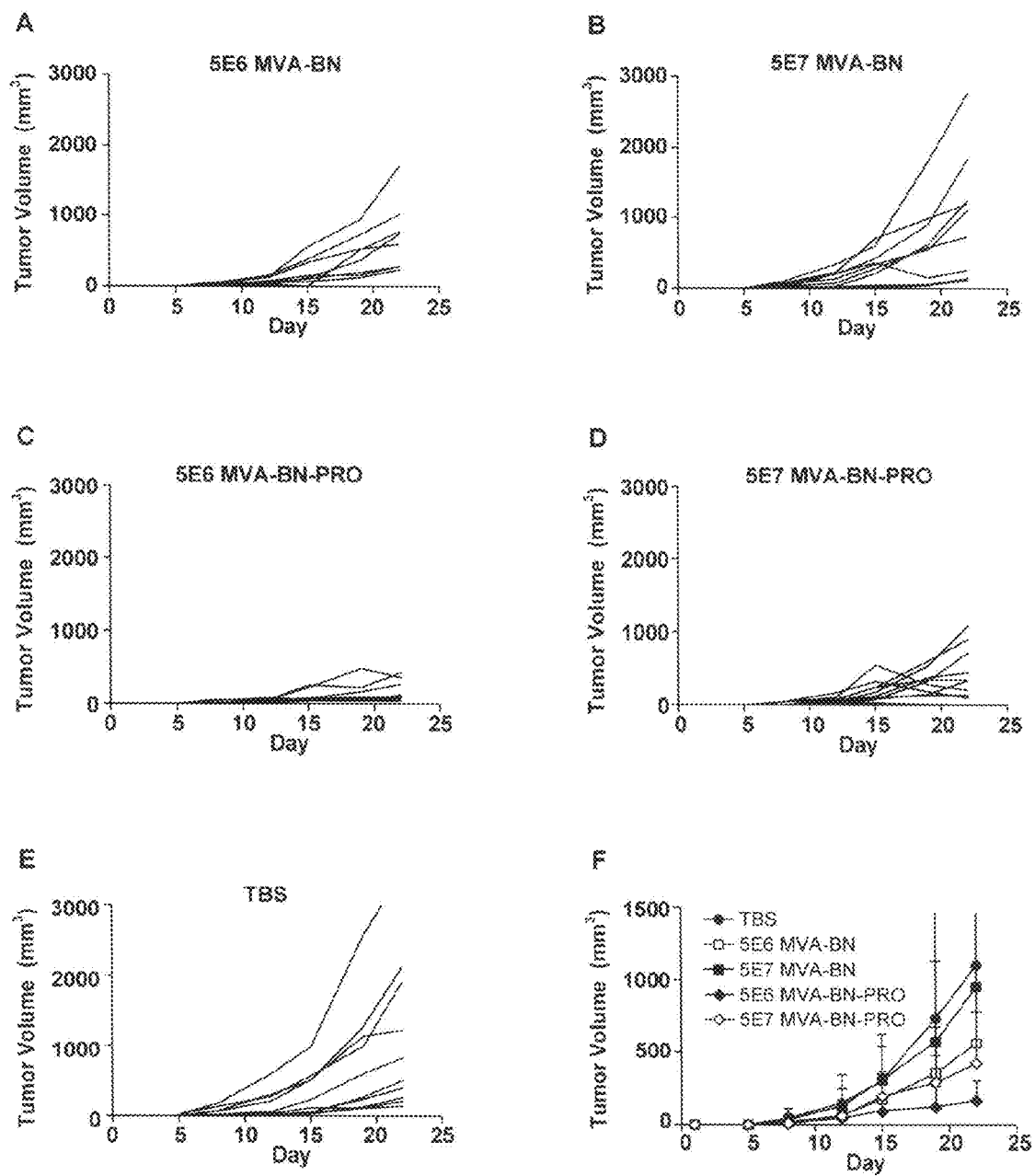
FIG. 9A-F. Therapeutic Suppression of Tumor Growth in Mice Treated with MVA-BN-PRO. BALB/c mice (10 animals in each group) were challenged with E6 cells ($1\times10^5$ cells injected id) on day 1 and treated subcutaneously on day 1, 8, and 15 either with TBS (E), MVA-BN® ($5\times10^6$ or $5\times10^7$ TCID$_{50}$; A and B), or MVA-BN-PRO ($5\times10^6$ or $5\times10^7$ TCID$_{50}$; C and D). Mice were sacrificed on day 22. Panels A-E show tumor sizes of individual mice. Averages of tumor sizes and standard deviations for each group are depicted in panel F. Tumor growth was measured twice weekly using calipers. Tumor volume was calculated as: $(L\times W^2)/2$. Error bars represent standard deviations (SD).

As shown in FIG. 9, the tumors in animals treated with MVA-BN-PRO (FIGS. 9C and 9D) grew significantly slower than tumors in MVA-BN®-(FIGS. 9A and 9B) or TBS-treated animals (FIG. 9E). In both, MVA-BN-PRO treatment groups, tumor size stabilization or regression was observed in 50% of the animals. FIG. 9F, shows the difference in mean tumor sizes between groups. The average tumor volume was statistically significantly different between animals treated with $5\times10^6$ $TCID_{50}$ MVA-BN-PRO and TBS- or MVA-BN®-treated control groups (p=0.014 and p=0.032, respectively) whereas statistical significance was not reached between the $5\times10^7$ $TCID_{50}$ MVA-BN-PRO-treated group and TBS control group (p=0.07). These data show that treatment of mice with MVA-BN-PRO inhibits the growth of prostate tumors in mice in the therapeutic setting.

Figure 10:
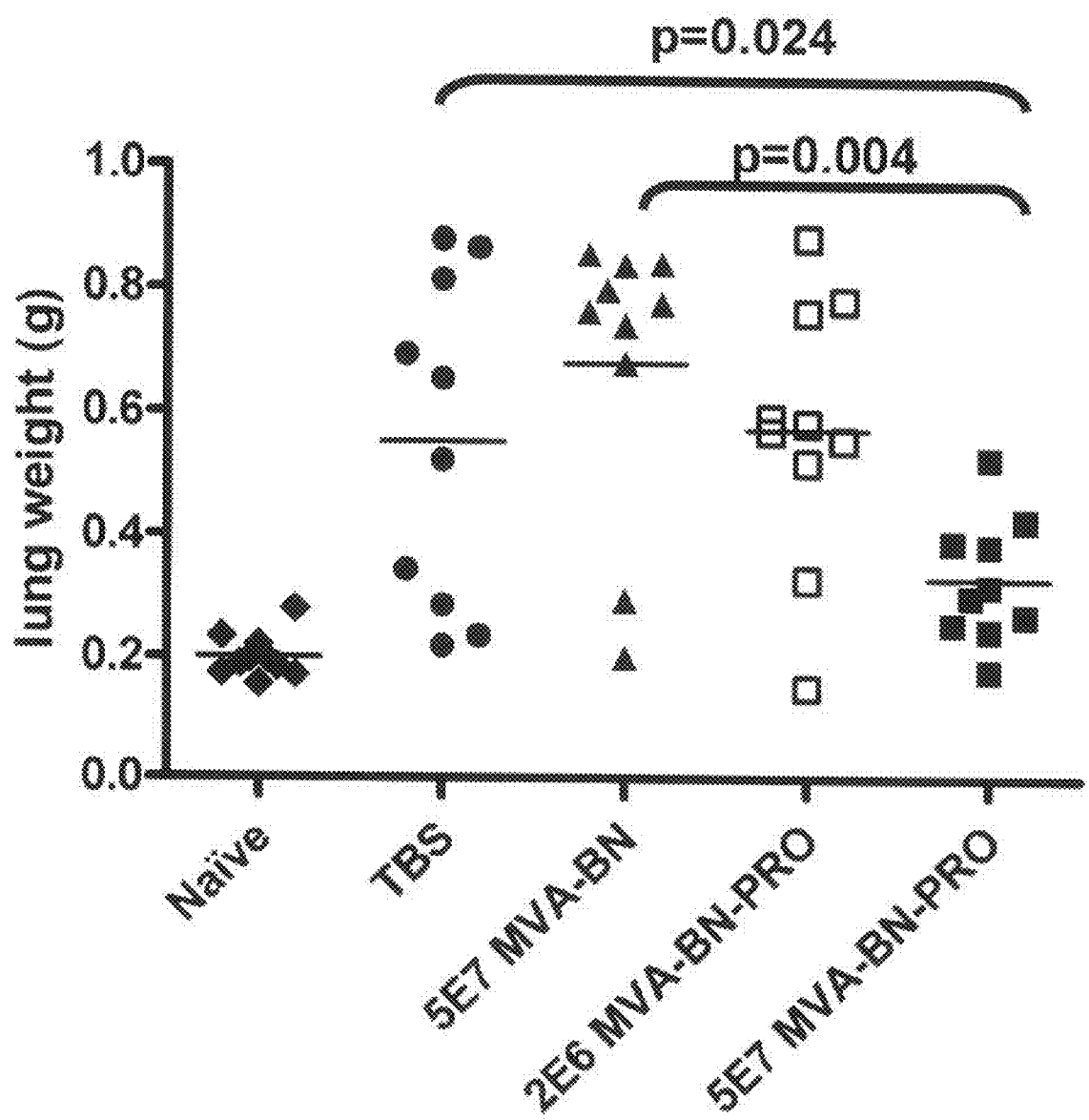
FIG. 10. Suppression of PAP-positive Tumor Growth in Mice Treated with MVA-BN-PRO. BALB/c mice (10 animals in each group) were challenged with CT26-PAP ($5\times10^5$ cells injected intravenously) on Day 1 and treated intraperitonally on Day 4 either with TBS, MVA-BN ($5\times10^7$ TCID$_{50}$), or MVA-BN-PRO ($2\times10^6$ and $5\times10^7$ TCID$_{50}$). Mice were sacrificed on Day 14 and their lungs weighed. Data points represent the lung weight of individual mice. Horizontal bar indicate the mean of lung weight for each group.

The ability of MVA-BN-PRO to also suppress established PAP-expressing tumors was evaluated in an experimental lung metastasis model using CT26 cells stably expressing human PAP. CT26 is a chemically induced colorectal carcinoma of BALB/c mice (Brattain et al., 1980). In this model, CT26-PAP cells are injected intravenously into BALB/c mice and tumor burden is assessed in the lungs where tumor nodules grow. Mice were challenged with CT26-PAP ($5\times10^5$) cells injected intravenously on Day 1 and treated intraperiotenally on Day 4 with a single injection of TBS, MVA-BN ($5\times10^7$ $TCID_{50}$) or MVA-BN-PRO ($2\times10^6$ and $5\times10^7$ $TCID_{50}$). Mice were then sacrificed on Day 14 and their lungs were weighed. As shown in FIG. 10, the tumor burden in mice treated with $5\times10^7$ $TCID_{50}$ MVA-BN-PRO was significantly lower than in control mice (p<0.024); This anti-tumor activity was dose-dependent since the lower dose of MVA-BN-PRO had no effect. Furthermore, this anti-tumor activity was most likely mediated by PAP-specific immune response as tumor burden in mice of the control and MVA-BN treated groups was unchanged.

These data demonstrate that treatment of mice with MVA-BN-PRO inhibits the growth of established PAP-positive tumors in mice. Thus, both PSA and PAP prostate antigens encoded by MVA-BN-PRO contribute to the induction of

Example 5

Immunogenicity of MVA-BN-PRO Across Haplotype Restriction

Immune responses results from the interaction of antigen-derived epitopes with polymorphic antigen-presenting molecules on immune competent cells. A benefit of the two tumor antigens in MVA-BN-PRO is that they potentially increase the number of tumor antigen-derived epitopes that can interact with antigen-presenting molecules of various haplotypes. Consequently, it is anticipated that MVA-BN-PRO will be immunogenic in individuals with a broader range of haplotypes than vaccines containing a single antigen. This possibility was evaluated in preclinical models using animals with different haplotypes. In this example, the vector described in Example 1 was modified to replace the ATI promoter by an early/late synthetic promoter (Ps; Chakrabarti S, Sisler J R, and Moss B, BioTechniques 23: 1094-1097 (December 1997)). Consequently, the PSA and PAP protein should be expressed with other early and late genes throughout the complete MVA infectious phase.

Sequence of the Ps Promoter:

```
                                         (SEQ ID NO: 6)
5'-AAAAAATTGAAATTTTATTTTTTTTTTGGAATATAAATAAT
```

Figure 11:
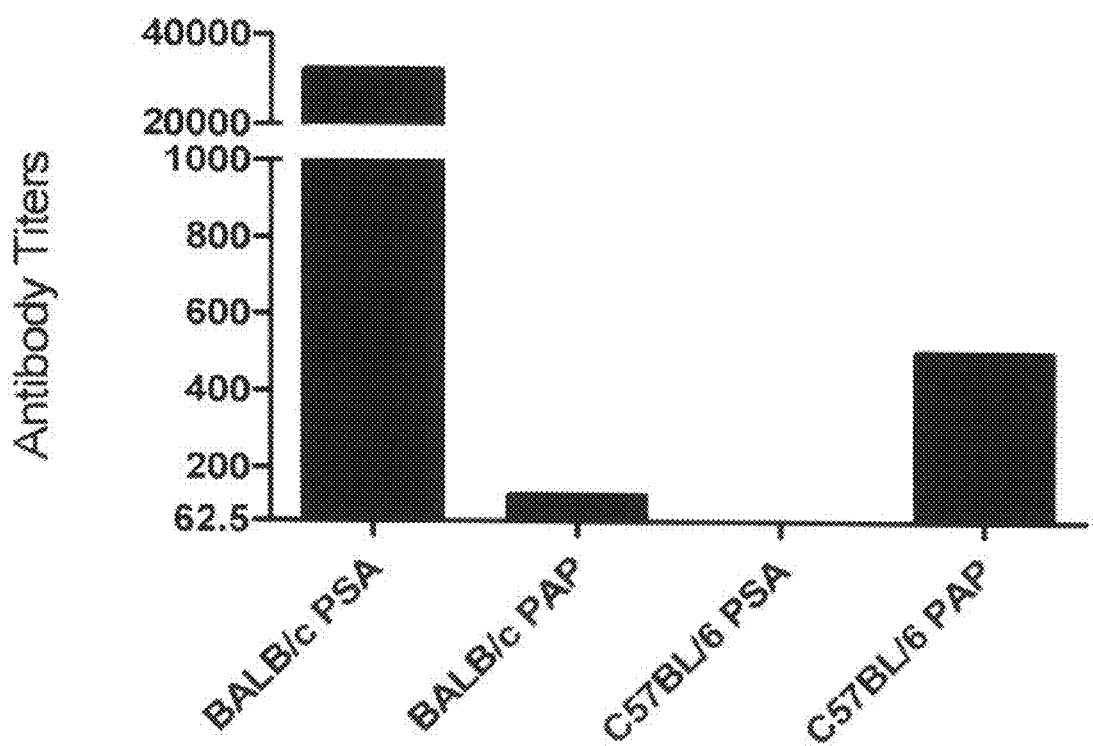
FIG. 11. Anti-PSA and anti-PAP antibody responses induced in BALB/c or C57BL/6 mice. Male BALB/c and C57BL/6 mice (5 animals in each group) were immunized on days 1, 15, and 29 with $5\times10^7$ TCID$_{50}$ of MVA-BN-PRO. Blood samples were collected on day 42, and serial dilutions of pooled sera were analyzed for the presence of anti-PSA or anti-PAP IgG by ELISA. Titers were calculated as the reciprocal value of the last dilution with an O.D. at least 2-fold higher than background (defined as serum at the same dilution from TBS treated animals). Data points for sera with titers below the lowest dilution tested (<125) were arbitrarily placed on the x-axis positioned one dilution below the first dilution of the assay (62.5) for graphing purposes.

Male BALB/c and C57BL/6 mice (5 animals in each group) were immunized on days 1, 15, and 29 with $5 \times 10^7$ TCID$_{50}$ of MVA-BN-PRO. Blood samples were collected on day 42, and serial dilutions of pooled sera were analyzed for the presence of anti-PSA or anti-PAP IgG by ELISA as described in Example 3. As shown in FIG. 11, high titers of anti-PSA antibodies were detected in sera from BALB/c mice only. In contrast, although anti-PAP antibody titers were measured in sera from both mouse strains, higher anti-PAP antibody titers were detected in serum from C57BL/6 mice. This data emphasizes the haplotype relationship of the immune response for specific antigens and support the idea that multiple tumor antigens in MVA-BN-PRO should provide effective immunity in a broader range of individuals with different haplotypes.

Example 6

Safety and Immunogenicity of MVA-BN-PRO in Humans

MVA-BN-PRO is currently under investigation for the treatment of patients with prostate cancer. At the time of this application, 4 patients received 1 to 3 treatments with 1E8 TCID50 of MVA-BN-PRO with no reported adverse effects. MVA-BN-PRO immunogenicity in one of these patients was evaluated by comparing the T cell responses to PSA and PAP pre- and post-treatment. The presence of antigen-specific gamma interferon (IFN-γ) secreting T-cells in patient peripheral blood mononuclear cells (PBMC) was determined using an ELISpot assay. Responses were determined prior to treatment (Base) and 2 weeks after the third subcutaneous vaccination with $10^8$ TCID$_{50}$ of MVA-BN-PRO (TC3). Patient PBMC ($2 \times 10^5$) in MATIS-10% media (RPMI, Click's medium, 10% Human AB serum, 0.5M 2-β-Mercaptoethanol, and 2% Penicillin/Streptomycin) were transferred to hydrated wells of Multiscreen 96-well PVDF plates (Millipore, Cat. No. MSIPS4510) pre-coated with an anti-human IFN-γ capture antibody (Mabtech, clone MAb 1D1K, Cat. No. 3420-3) at 10 µg/mL. Subsequently, PBMC were stimulated with either PSA at 5 µg/mL (Biodesign Cat. No. A86878H), a 11-mer overlapping library of 63 15-mer peptides (OPL) derived from PSA full-length sequence at 63 µM (1 µM per peptide), PAP at 1 µg/mL (Biodesign, Cat. No. A81277H), a 11-mer OPL of 94 15-mer peptides derived from PAP full-length sequence at 94 µM (1 µM per peptide), a pool of 44 MHC Class I peptide derived from 10 prostate cancer tumor associated antigens (TAA) at 44 µM (1 µM per peptide), a pool of 15 15 MHC Class II peptides derived from 5 prostate cancer TAA at 15 µM (1 µM per peptide), or MVA (Bavarian Nordic, MVA-BN-PROD05A06-C) at a multiplicity of infection (MOI) of 10.

Sequence of the 63 peptides of PSA OPL:

| Peptide | Position |
|---|---|
| MWVPVVFLTLSVTWI | (a.a. 1-15 of SEQ ID NO: 3) |
| VVFLTLSVTWIGAAP | (a.a. 5-19 of SEQ ID NO: 3) |
| TLSVTWIGAAPLILS | (a.a. 9-23 of SEQ ID NO: 3) |
| TWIGAAPLILSRIVG | (a.a. 13-27 of SEQ ID NO: 3) |
| AAPLILSRIVGGWEC | (a.a. 17-31 of SEQ ID NO: 3) |
| ILSRIVGGWECEKHS | (a.a. 21-35 of SEQ ID NO: 3) |
| IVGGWECEKHSQPWQ | (a.a. 25-39 of SEQ ID NO: 3) |
| WECEKHSQPWQVLVA | (a.a. 29-43 of SEQ ID NO: 3) |
| KHSQPWQVLVASRGR | (a.a. 33-47 of SEQ ID NO: 3) |
| PWQVLVASRGRAVCG | (a.a. 37-51 of SEQ ID NO: 3) |
| LVASRGRAVCGGVLV | (a.a. 41-55 of SEQ ID NO: 3) |
| RGRAVCGGVLVHPQW | (a.a. 45-59 of SEQ ID NO: 3) |
| VCGGVLVHPQWVLTA | (a.a. 49-63 of SEQ ID NO: 3) |
| VLVHPQWVLTAAHCI | (a.a. 53-67 of SEQ ID NO: 3) |
| PQWVLTAAHCIRNKS | (a.a. 57-71 of SEQ ID NO: 3) |
| LTAAHCIRNKSVILL | (a.a. 61-75 of SEQ ID NO: 3) |
| HCIRNKSVILLGRHS | (a.a. 65-79 of SEQ ID NO: 3) |
| NKSVILLGRHSLFHP | (a.a. 69-83 of SEQ ID NO: 3) |
| ILLGRHSLFHPEDTG | (a.a. 73-87 of SEQ ID NO: 3) |
| RHSLFHPEDTGQVFQ | (a.a. 77-91 of SEQ ID NO: 3) |
| FHPEDTGQVFQVSHS | (a.a. 81-95 of SEQ ID NO: 3) |
| DTGQVFQVSHSFPHP | (a.a. 85-99 of SEQ ID NO: 3) |
| VFQVSHSFPHPLYDM | (a.a. 89-103 of SEQ ID NO: 3) |
| SHSFPHPLYDMSLLK | (a.a. 93-107 of SEQ ID NO: 3) |
| PHPLYDMSLLKNRFL | (a.a. 97-111 of SEQ ID NO: 3) |
| YDMSLLKNRFLRPGD | (a.a. 101-115 of SEQ ID NO: 3) |
| LLKNRFLRPGDDSSH | (a.a. 105-119 of SEQ ID NO: 3) |
| RFLRPGDDSSHDLML | (a.a. 109-123 of SEQ ID NO: 3) |
| PGDDSSHDLMLLRLS | (a.a. 113-127 of SEQ ID NO: 3) |
| SSHDLMLLRLSEPAE | (a.a. 117-131 of SEQ ID NO: 3) |

| | | | |
|---|---|---|---|
| LMLLRLSEPAELTDA | (a.a. 121-135 of SEQ ID NO: 3) | LLFFWLDRSVLAKEL | (a.a. 21-35 of SEQ ID NO: 4) |
| RLSEPAELTDAVKVM | (a.a. 125-139 of SEQ ID NO: 3) | WLDRSVLAKELKFVT | (a.a. 25-39 of SEQ ID NO: 4) |
| PAELTDAVKVMDLPT | (a.a. 129-143 of SEQ ID NO: 3) | SVLAKELKFVTLVFR | (a.a. 29-43 of SEQ ID NO: 4) |
| TDAVKVMDLPTQEPA | (a.a. 133-147 of SEQ ID NO: 3) | KELKFVTLVFRHGDR | (a.a. 33-47 of SEQ ID NO: 4) |
| KVMDLPTQEPALGTT | (a.a. 137-151 of SEQ ID NO: 3) | FVTLVFRHGDRSPID | (a.a. 37-51 of SEQ ID NO: 4) |
| LPTQEPALGTTCYAS | (a.a. 141-155 of SEQ ID NO: 3) | VFRHGDRSPIDTFPT | (a.a. 41-55 of SEQ ID NO: 4) |
| EPALGTTCYASGWGS | (a.a. 145-159 of SEQ ID NO: 3) | GDRSPIDTFPTDPIK | (a.a. 45-59 of SEQ ID NO: 4) |
| GTTCYASGWGSIEPE | (a.a. 149-163 of SEQ ID NO: 3) | PIDTFPTDPIKESSW | (a.a. 49-63 of SEQ ID NO: 4) |
| YASGWGSIEPEEFLT | (a.a. 153-167 of SEQ ID NO: 3) | FPTDPIKESSWPQGF | (a.a. 53-67 of SEQ ID NO: 4) |
| WGSIEPEEFLTPKKL | (a.a. 157-171 of SEQ ID NO: 3) | PIKESSWPQGFGQLT | (a.a. 57-71 of SEQ ID NO: 4) |
| EPEEFLTPKKLQCVD | (a.a. 161-175 of SEQ ID NO: 3) | SSWPQGFGQLTQLGM | (a.a. 61-75 of SEQ ID NO: 4) |
| FLTPKKLQCVDLHVI | (a.a. 165-179 of SEQ ID NO: 3) | QGFGQLTQLGMEQHY | (a.a. 65-79 of SEQ ID NO: 4) |
| KKLQCVDLHVISNDV | (a.a. 169-183 of SEQ ID NO: 3) | QLTQLGMEQHYELGE | (a.a. 69-83 of SEQ ID NO: 4) |
| CVDLHVISNDVCAQV | (a.a. 173-187 of SEQ ID NO: 3) | LGMEQHYELGEYIRK | (a.a. 74-87 of SEQ ID NO: 4) |
| HVISNDVCAQVHPQK | (a.a. 177-191 of SEQ ID NO: 3) | QHYELGEYIRKRYRK | (a.a. 77-91 of SEQ ID NO: 4) |
| NDVCAQVHPQKVTKF | (a.a. 181-195 of SEQ ID NO: 3) | LGEYIRKRYRKFLNE | (a.a. 81-95 of SEQ ID NO: 4) |
| AQVHPQKVTKFMLCA | (a.a. 185-199 of SEQ ID NO: 3) | IRKRYRKFLNESYKH | (a.a. 85-99 of SEQ ID NO: 4) |
| PQKVTKFMLCAGRWT | (a.a. 189-203 of SEQ ID NO: 3) | YRKFLNESYKHEQVY | (a.a. 89-103 of SEQ ID NO: 4) |
| TKFMLCAGRWTGGKS | (a.a. 193-207 of SEQ ID NO: 3) | LNESYKHEQVYIRST | (a.a. 93-107 of SEQ ID NO: 4) |
| LCAGRWTGGKSTCSG | (a.a. 197-211 of SEQ ID NO: 3) | YKHEQVYIRSTDVDR | (a.a. 97-111 of SEQ ID NO: 4) |
| RWTGGKSTCSGDSGG | (a.a. 201-215 of SEQ ID NO: 3) | QVYIRSTDVDRTLMS | (a.a. 101-115 of SEQ ID NO: 4) |
| GKSTCSGDSGGPLVC | (a.a. 205-219 of SEQ ID NO: 3) | RSTDVDRTLMSAMTN | (a.a. 105-119 of SEQ ID NO: 4) |
| CSGDSGGPLVCNGVL | (a.a. 209-223 of SEQ ID NO: 3) | VDRTLMSAMTNLAAL | (a.a. 109-123 of SEQ ID NO: 4) |
| SGGPLVCNGVLQGIT | (a.a. 213-227 of SEQ ID NO: 3) | LMSAMTNLAALFPPE | (a.a. 113-127 of SEQ ID NO: 4) |
| LVCNGVLQGITSWGS | (a.a. 217-231 of SEQ ID NO: 3) | MTNLAALFPPEGVSI | (a.a. 117-131 of SEQ ID NO: 4) |
| GVLQGITSWGSEPCA | (a.a. 221-235 of SEQ ID NO: 3) | AALFPPEGVSIWNPI | (a.a. 121-135 of SEQ ID NO: 4) |
| GITSWGSEPCALPER | (a.a. 225-239 of SEQ ID NO: 3) | PPEGVSIWNPILLWQ | (a.a. 125-139 of SEQ ID NO: 4) |
| WGSEPCALPERPSLY | (a.a. 229-243 of SEQ ID NO: 3) | VSIWNPILLWQPIPV | (a.a. 129-143 of SEQ ID NO: 4) |
| PCALPERPSLYTKVV | (a.a. 233-247 of SEQ ID NO: 3) | NPILLWQPIPVHTVP | (a.a. 133-147 of SEQ ID NO: 4) |
| PERPSLYTKVVHYRK | (a.a. 237-251 of SEQ ID NO: 3) | LWQPIPVHTVPLSED | (a.a. 137-151 of SEQ ID NO: 4) |
| SLYTKVVHYRKWIKD | (a.a. 241-255 of SEQ ID NO: 3) | IPVHTVPLSEDQLLY | (a.a. 141-155 of SEQ ID NO: 4) |
| KVVHYRKWIKDTIVA | (a.a. 245-259 of SEQ ID NO: 3) | TVPLSEDQLLYLPFR | (a.a. 145-159 of SEQ ID NO: 4) |
| YRKWIKDTIVANP | (a.a. 249-261 of SEQ ID NO: 3) | SEDQLLYLPFRNCPR | (a.a. 149-163 of SEQ ID NO: 4) |

Sequence of the 94 peptides of PAP OPL:

| | | | |
|---|---|---|---|
| | | LLYLPFRNCPRFQEL | (a.a. 153-167 of SEQ ID NO: 4) |
| | | PFRNCPRFQELESET | (a.a. 157-171 of SEQ ID NO: 4) |
| MRAAPLLLARAASLS | (a.a. 1-15 of SEQ ID NO: 4) | CPRFQELESETLKSE | (a.a. 161-175 of SEQ ID NO: 4) |
| PLLLARAASLSLGFL | (a.a. 5-19 of SEQ ID NO: 4) | QELESETLKSEEFQK | (a.a. 165-179 of SEQ ID NO: 4) |
| ARAASLSLGFLFLLF | (a.a. 9-23 of SEQ ID NO: 4) | SETLKSEEFQKRLHP | (a.a. 169-183 of SEQ ID NO: 4) |
| SLSLGFLFLLFFWLD | (a.a. 13-27 of SEQ ID NO: 4) | KSEEFQKRLHPYKDF | (a.a. 173-187 of SEQ ID NO: 4) |
| GFLFLLFFWLDRSVL | (a.a. 17-31 of SEQ ID NO: 4) | FQKRLHPYKDFIATL | (a.a. 177-191 of SEQ ID NO: 4) |

-continued

| | |
|---|---|
| LHPYKDFIATLGKLS | (a.a. 181-195 of SEQ ID NO: 4) |
| KDFIATLGKLSGLHG | (a.a. 185-199 of SEQ ID NO: 4) |
| ATLGKLSGLHGQDLF | (a.a. 189-203 of SEQ ID NO: 4) |
| KLSGLHGQDLFGIWS | (a.a. 193-207 of SEQ ID NO: 4) |
| LHGQDLFGIWSKVYD | (a.a. 197-211 of SEQ ID NO: 4) |
| DLFGIWSKVYDPLYC | (a.a. 201-215 of SEQ ID NO: 4) |
| IWSKVYDPLYCESVH | (a.a. 205-219 of SEQ ID NO: 4) |
| VYDPLYCESVHNFTL | (a.a. 209-223 of SEQ ID NO: 4) |
| LYCESVHNFTLPSWA | (a.a. 213-227 of SEQ ID NO: 4) |
| SVHNFTLPSWATEDT | (a.a. 217-231 of SEQ ID NO: 4) |
| FTLPSWATEDTMTKL | (a.a. 221-235 of SEQ ID NO: 4) |
| SWATEDTMTKLRELS | (a.a. 225-239 of SEQ ID NO: 4) |
| EDTMTKLRELSELSL | (a.a. 229-243 of SEQ ID NO: 4) |
| TKLRELSELSLLSLY | (a.a. 234-247 of SEQ ID NO: 4) |
| ELSELSLLSLYGIHK | (a.a. 237-251 of SEQ ID NO: 4) |
| LSLLSLYGIHKQKEK | (a.a. 241-255 of SEQ ID NO: 4) |
| SLYGIHKQKEKSRLQ | (a.a. 245-259 of SEQ ID NO: 4) |
| IHKQKEKSRLQGGVL | (a.a. 249-263 of SEQ ID NO: 4) |
| KEKSRLQGGVLVNEI | (a.a. 253-267 of SEQ ID NO: 4) |
| RLQGGVLVNEILNHM | (a.a. 257-271 of SEQ ID NO: 4) |
| GVLVNEILNHMKRAT | (a.a. 261-275 of SEQ ID NO: 4) |
| NEILNHMKRATQIPS | (a.a. 265-279 of SEQ ID NO: 4) |
| NHMKRATQIPSYKKL | (a.a. 269-283 of SEQ ID NO: 4) |
| RATQIPSYKKLIMYS | (a.a. 274-287 of SEQ ID NO: 4) |
| IPSYKKLIMYSAHDT | (a.a. 277-291 of SEQ ID NO: 4) |
| KKLIMYSAHDTTVSG | (a.a. 281-295 of SEQ ID NO: 4) |
| MYSAHDTTVSGLQMA | (a.a. 285-299 of SEQ ID NO: 4) |
| HDTTVSGLQMALDVY | (a.a. 289-303 of SEQ ID NO: 4) |
| VSGLQMALDVYNGLL | (a.a. 293-307 of SEQ ID NO: 4) |
| QMALDVYNGLLPPYA | (a.a. 297-311 of SEQ ID NO: 4) |
| DVYNGLLPPYASCHL | (a.a. 301-315 of SEQ ID NO: 4) |
| GLLPPYASCHLTELY | (a.a. 305-319 of SEQ ID NO: 4) |
| PYASCHLTELYFEKG | (a.a. 309-323 of SEQ ID NO: 4) |
| CHLTELYFEKGEYFV | (a.a. 313-327 of SEQ ID NO: 4) |
| ELYFEKGEYFVEMYY | (a.a. 317-331 of SEQ ID NO: 4) |
| EKGEYFVEMYYRNET | (a.a. 321-335 of SEQ ID NO: 4) |
| YFVEMYYRNETQHEP | (a.a. 325-339 of SEQ ID NO: 4) |
| MYYRNETQHEPYPLM | (a.a. 329-343 of SEQ ID NO: 4) |
| NETQHEPYPLMLPGC | (a.a. 333-347 of SEQ ID NO: 4) |
| HEPYPLMLPGCSPSC | (a.a. 337-351 of SEQ ID NO: 4) |
| PLMLPGCSPSCPLER | (a.a. 341-355 of SEQ ID NO: 4) |
| PGCSPSCPLERFAEL | (a.a. 345-359 of SEQ ID NO: 4) |
| PSCPLERFAELVGPV | (a.a. 349-363 of SEQ ID NO: 4) |
| LERFAELVGPVIPQD | (a.a. 353-367 of SEQ ID NO: 4) |
| AELVGPVIPQDWSTE | (a.a. 357-371 of SEQ ID NO: 4) |
| GPVIPQDWSTECMTT | (a.a. 361-375 of SEQ ID NO: 4) |
| PQDWSTECMTTNSHQ | (a.a. 365-379 of SEQ ID NO: 4) |
| STECMTTNSHQGTED | (a.a. 369-383 of SEQ ID NO: 4) |
| MTTNSHQGTEDSTD | (a.a. 373-386 of SEQ ID NO: 4) |

Sequence of the 44 TAA MHC Class I peptides with corresponding TAA and position in TAA sequence:

| Peptides | Sequence |
|---|---|
| PSMA | |
| 4-12 | LLHETDSAV (a.a. 4-12 of SEQ ID NO: 7) |
| 109-117 | ELAHYDVLL (a.a. 109-117 of SEQ ID NO: 7) |
| 168-176 | PSLYTKVVHY (a.a. 168-176 of SEQ ID NO: 7) |
| 173-181 | DLVYVNYAR (a.a. 173-181 of SEQ ID NO: 7) |
| 178-186 | NYARTEDFF (a.a. 178-186 of SEQ ID NO: 7) |
| 199-207 | KIVIARYGK (a.a. 199-207 of SEQ ID NO: 7) |
| 207-215 | KVFRGNKVK (a.a. 207-215 of SEQ ID NO: 7) |
| 227-235 | LYSDPADYF (a.a. 227-235 of SEQ ID NO: 7) |
| 260-268 | NLNGAGDPL (a.a. 260-268 of SEQ ID NO: 7) |
| 347-356 | HSTNGVTRIY (a.a. 347-356 of SEQ ID NO: 7) |
| 354-363 | RIYNVIGTLR (a.a. 354-363 of SEQ ID NO: 7) |
| 403-411 | GTLKKEGWR (a.a. 403-411 of SEQ ID NO: 7) |
| 431-440 | STEWAEENSR (a.a. 431-440 of SEQ ID NO: 7) |
| 441-450 | LLQERGVAYI (a.a. 441-450 of SEQ ID NO: 7) |
| 461-469 | TLRVDCTPL (a.a. 461-469 of SEQ ID NO: 7) |
| 557-566 | ETYELVEKFY (a.a. 557-566 of SEQ ID NO: 7) |

-continued

| Peptides | Sequence |
|---|---|
| 641-649 | EIASKFSER (a.a. 641-649 of SEQ ID NO: 7) |
| 663-671 | MMNDQLMFL (a.a. 663-671 of SEQ ID NO: 7) |
| 680-688 | GLPDRPFYR (a.a. 680-688 of SEQ ID NO: 7) |
| 711-719 | ALFDIESKV (a.a. 711-719 of SEQ ID NO: 7) |
| PSCA | |
| 7-15 | ALLMAGLAL (a.a. 7-15 of SEQ ID NO: 8) |
| 14-22 | ALQPGTALL (a.a. 14-22 of SEQ ID NO: 8) |
| 21-30 | LLCYSCKAQV (a.a. 21-30 of SEQ ID NO: 8) |
| 76-84 | DYYVGKKNI (a.a. 76-84 of SEQ ID NO: 8) |
| 108-116 | ALLPALGLL (a.a. 108-116 of SEQ ID NO: 8) |
| 109-117 | LLPALGLLL (a.a. 109-117 of SEQ ID NO: 8) |
| 115-123 | LLLWGPGQ (a.a. 115-123 of SEQ ID NO: 8) |
| STEAP1 | |
| 86-94 | FLYTLLREV (a.a. 86-94 of SEQ ID NO: 9) |
| 102-116 | HQQYFYKIPILVINK (a.a. 102-116 of SEQ ID NO: 9) |
| 262-270 | LLLGTIHAL (a.a. 262-270 of SEQ ID NO: 9) |
| 292-300 | MIAVFLPIV (a.a. 292-300 of SEQ ID NO: 9) |
| PTHrp | |
| 42-51 | QLLHDKGKS (a.a. 42-51 of SEQ ID NO: 10) |
| 59-68 | FLHHLIAEIH (a.a. 59-68 of SEQ ID NO: 10) |
| 59-65 | FLHHLIA (a.a. 59-65 of SEQ ID NO: 10) |
| 165-173 | TSTTSLELD (a.a. 165-173 of SEQ ID NO: 10) |
| TARP | |
| 4-13 | FPPSPLFFFL (a.a. 4-13 of SEQ ID NO: 11) |
| 27-35 | FVFLRNFSL (a.a. 27-35 of SEQ ID NO: 11) |
| 29-37 | FLRNFSLML (a.a. 29-37 of SEQ ID NO: 11) |

-continued

| Peptides | Sequence |
|---|---|
| Prostein | |
| 31-39 | CLAAGITYV (SEQ ID NO: 12) |
| Eph | |
| 58-66 | IMNDMPIYM (SEQ ID NO: 13) |
| 550-558 | VLAGVGFFI (SEQ ID NO: 14) |
| Survivin | |
| 96-104 | LTLGEFLKL (SEQ ID NO: 15) |
| hTERT | |
| 973-981 | KLFGVLRLK (SEQ ID NO: 16) |
| HER2 | |
| 665-673 | VVLGVVFGI (SEQ ID NO: 17) |

Sequence of the 15 TAA MHC Class II peptides with corresponding TAA and position in TAA sequence

| Kallikrein 4 | |
|---|---|
| 125-139 | SVSESDTIRSISIAS (SEQ ID NO: 18) |
| 155-169 | LLANGRMPTVLQCVN (SEQ ID NO: 19) |
| 160-174 | RMPTVLQCVNVSVVS (SEQ ID NO: 20) |
| Histone H4 | |
| 14-28 | GAKRHRKVLRDNIQG (a.a. 14-28 of SEQ ID NO: 21) |
| 16-39 | KRHRKVLRDNIQGITKPAIRRLAR (a.a. 16-39 of SEQ ID NO: 21) |
| 31-45 | TKPAIRRLARRGGVK (a.a. 31-45 of SEQ ID NO: 21) |
| 49-63 | LIYEETRGVLKVFLE (a.a. 49-63 of SEQ ID NO: 21) |
| 71-94 | TYTEHAKRKTVTAMDVVYALKRQG (a.a. 71-94 of SEQ ID NO: 21) |
| TARP | |
| 1-14 | MQMFPPSPLFFFLQ (SEQ ID NO: 11) |
| 14-27 | QLLKQSSRRLEHTF (SEQ ID NO: 11) |
| ENAH (hMena) | |
| 502-510 | TMNGSKSPV (SEQ ID NO: 22) |

-continued

```
         PSMA
    334-348    TGNFSTQKVKMHIHS
               (a.a. 334-348 of SEQ ID NO: 7)

459-473    NYTLRVDCTPLMYSL
               (a.a. 459-473 of SEQ ID NO: 7)

687-701    YRHVIYAPSSHNKYA
               (a.a. 687-701 of SEQ ID NO: 7)

730-744    RQIYVAAFTVQAAAE
               (a.a. 730-744 SEQ ID NO: 7)
```

Figure 12:
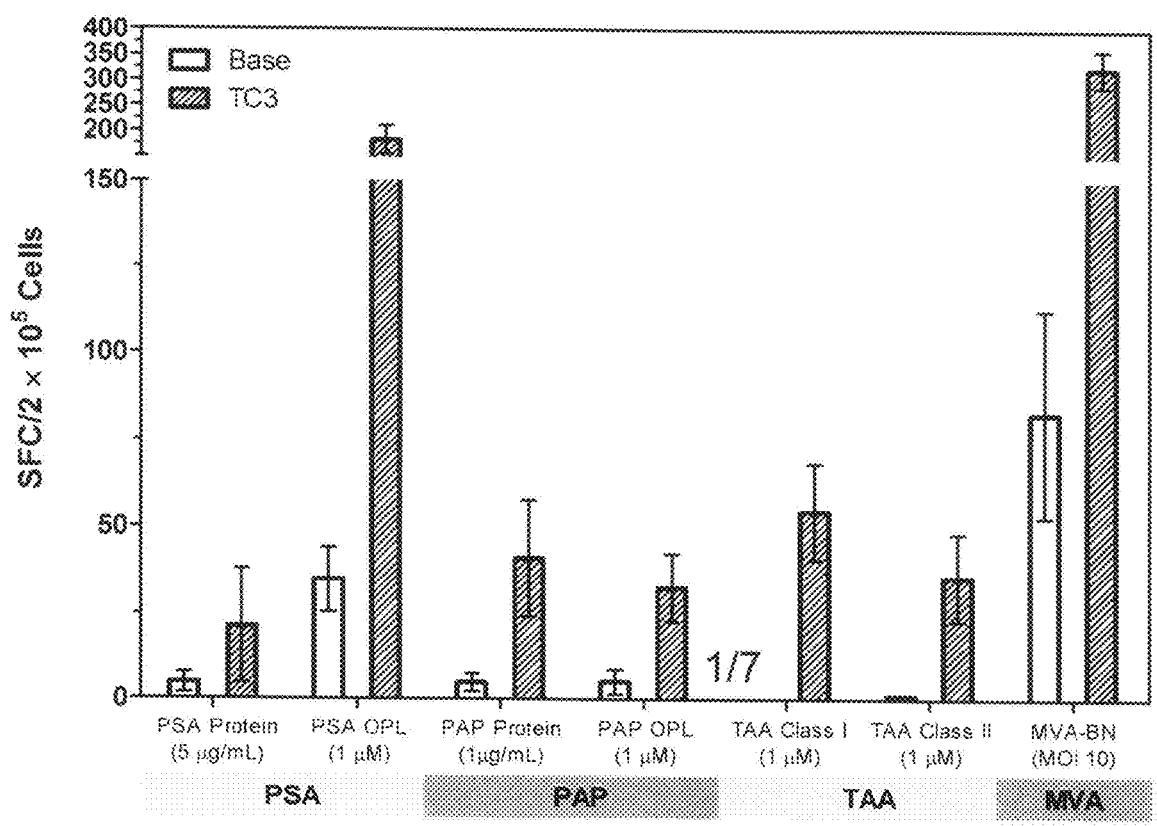
FIG. 12. T cell responses in Patient treated with MVA-BN-PRO. PBMC from blood of Patient J-D-1001 were collected pre-treatment (Base) or post-MVA-BN-PRO treatment (TC3). Cells were incubated for 40 hours with either PSA protein, PSA overlapping peptide library (OPL), PAP protein, PAP OPL, pools of MHC Class I and Class II peptides derived from tumor associated antigens (TAA) or MVA-BN at the concentration indicated on the graph. T cell activation was determined by ELISpot measuring secreted IFN-γ. For each stimulating condition, results are expressed as the mean IFN-γ spot forming cells (SFC) per $2\times10^5$ PBMC. SFC values were derived from the mean of quadruplicate wells with the background subtracted.

After 40 hours of incubation at 37° C., 5% CO2, IFN-γ secretion was detected with 1 μg/mL of the biotinylated anti-human IFN-γ antibody (Mabtech, clone MAb 7-B6-1, Cat. No. 3420-6) followed by the addition of Streptavidin-Alkaline Phosphatase (BD Pharmingen, Cat. No. 554065) diluted 1/5000. ELISpot plates were developed with the Vector Blue Substrate (Vector Lab Inc., Cat. No. SK-5300) and spots were enumerated with an automatic spot reader (Cellular Technology Ltd. ImmunoSpot S3B Analyzer and CTL ImmunoSpot 4.0 Professional software). As shown FIG. 12, a pre-existing T cell response to PSA was detected prior to MVA-BN-PRO treatment in Patient J-D-1001. Anti-PSA T cells increased significantly after treatment whereas anti-PAP T cells were detected after treatment only. This data indicates that MVA-BN-PRO is immunogenic in humans and that simultaneous induction of both anti-PSA and anti-PAP responses can be achieved. MVA-BN-PRO treatment also resulted in a strong T cell response to the vector MVA-BN. Most importantly, MVA-BN-PRO treatment also resulted in the spreading of T cell responses to other tumor antigens as illustrated by the production of IFN-γ by T cells stimulated with TAA MHC I and II peptide pools. This indicates that MVA-BN-PRO-induced immune responses led to the killing of tumor cells followed by the amplification of anti-tumor responses to other tumor antigens. Antigen spreading is an important event in the induction of anti-tumor protective immunity as it prevents tumor evasion to vaccine-induced responses. Hence, the ability of MVA-BN-PRO to mediate immune responses to two tumor antigens in humans is a property that provides an effective immunotherapy.

We claim:

1. A method for treating a human prostate cancer patient comprising administering to the human patient a recombinant modified vaccinia virus Ankara (MVA) encoding a polypeptide comprising a human prostate-specific antigen (PSA) antigen and a polypeptide comprising a human prostatic acid phosphatase (PAP) antigen.

2. The method of claim 1, wherein the MVA is modified vaccinia virus Ankara-Bavarian Nordic (MVA-BN).

3. The method of claim 1, wherein the MVA virus comprises the nucleotide sequences of SEQ ID NO:1 and SEQ ID NO:2.

4. The method of claim 1, wherein a nucleic acid molecule encoding the PSA antigen and the PAP antigen are inserted in the MVA intergenic region 014L/015L.

5. The method of claim 1, wherein the cancer is prostate cancer in the patient is of metastasis.

6. The method of claim 1, wherein the recombinant MVA is administered prior to a tumoricidal dose of a taxane.

7. The method of claim 1, wherein the recombinant MVA is administered at the same time as a tumoricidal dose of a taxane.

8. The method of claim 1, wherein the recombinant MVA is administered after a tumoricidal dose of a taxane.

9. The method of claim 6, wherein the taxane is docetaxel or paclitaxel.

10. The method of claim 8, wherein the taxane is docetaxel or paclitaxel.

11. The method of claim 1 comprising administering to the patient a priming dose of the recombinant MVA and administering one or more boosting doses of the recombinant MVA.

12. The method of claim 11, wherein a priming dose of $1 \times 10^8$ $TCID_{50}$ and two boosting doses of $2 \times 10^8$ and $4 \times 10^8$ $TCID_{50}$ are administered to the patient.

13. The method of claim 12, wherein the boosting doses are given at four and eight weeks after the priming dose.

* * * * *

UNITED STATES PATENT AND TRADEMARK OFFICE
CERTIFICATE OF CORRECTION

| | |
|---|---|
| PATENT NO. | : 7,867,483 B2 |
| APPLICATION NO. | : 12/253094 |
| DATED | : January 11, 2011 |
| INVENTOR(S) | : Alain Delcayre et al. |

It is certified that error appears in the above-identified patent and that said Letters Patent is hereby corrected as shown below:

At column 51, lines 51-52, delete the text "5. The method of claim 1, wherein the cancer is prostate cancer in the patient is of metastasis." and insert the following text --5. The method of claim 1, wherein the prostate cancer is metastatic.--

Signed and Sealed this
Seventh Day of June, 2011

David J. Kappos
*Director of the United States Patent and Trademark Office*